(12) United States Patent
Huth et al.

(10) Patent No.: US 10,842,372 B2
(45) Date of Patent: Nov. 24, 2020

(54) FAST ABSOLUTE-REFLECTANCE METHOD FOR THE DETERMINATION OF TEAR FILM LIPID LAYER THICKNESS

(71) Applicant: Johnson & Johnson Surgical Vision, Inc., Santa Ana, CA (US)

(72) Inventors: Stan Huth, Newport Beach, CA (US); Denise Tran, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 16/531,679

(22) Filed: Aug. 5, 2019

(65) Prior Publication Data
US 2019/0350453 A1   Nov. 21, 2019

Related U.S. Application Data

(63) Continuation of application No. 14/298,176, filed on Jun. 6, 2014, now Pat. No. 10,368,738.

(51) Int. Cl.
*A61B 3/10*   (2006.01)

(52) U.S. Cl.
CPC .................. *A61B 3/101* (2013.01)

(58) Field of Classification Search
CPC ....... A61B 3/00; A61B 3/0008; A61B 3/0016; A61B 3/0025; A61B 3/0066; A61B 5/107; A61B 5/103; A61B 5/1071; A61B 5/1072; A61B 5/1075
See application file for complete search history.

(56) References Cited

U.S. PATENT DOCUMENTS

| 4,670,178 A | 6/1987 | Huth et al. |
| RE32,672 E | 5/1988 | Huth et al. |
| 5,045,704 A | 9/1991 | Coates |
| 6,236,459 B1 | 5/2001 | Negahdaripour et al. |
| 6,916,096 B2 | 7/2005 | Eberl et al. |
| 7,281,801 B2 | 10/2007 | Wang |
| 7,758,190 B2 | 7/2010 | Korb et al. |
| 7,866,819 B2 | 1/2011 | Tuan |
| 7,963,522 B2 | 6/2011 | Hoover |
| 8,192,026 B2 | 6/2012 | Gravely et al. |
| 8,585,204 B2 | 11/2013 | Gravely et al. |
| 8,591,033 B2 | 11/2013 | Korb et al. |
| 8,602,557 B2 | 12/2013 | Huth et al. |
| 9,456,741 B2 | 10/2016 | Huth et al. |

(Continued)

FOREIGN PATENT DOCUMENTS

| WO | 0026614 | 5/2000 |
| WO | 2013163367 A1 | 10/2013 |

OTHER PUBLICATIONS

Examination Report for European Patent Application No. 15735765. 8, dated Feb. 1, 2018, 4 pages.

(Continued)

*Primary Examiner* — Robert E. Tallman

(57) ABSTRACT

A method of determining tear film lipid layer thickness. The method includes the steps of measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; and comparing the calculated absolute reflectance spectrum to a theoretical absolute lipid reflectance spectrum to determine a tear film lipid layer thickness.

21 Claims, 10 Drawing Sheets

(56) References Cited

U.S. PATENT DOCUMENTS

| | | | |
|---|---|---|---|
| 9,610,011 | B2 | 4/2017 | Huth et al. |
| 9,681,802 | B2 | 6/2017 | Huth et al. |
| 10,117,571 | B2 | 11/2018 | Huth et al. |
| 10,368,738 | B2 | 8/2019 | Huth et al. |
| 2004/0212781 | A1 | 10/2004 | Mihashi et al. |
| 2006/0109423 | A1 | 5/2006 | Wang |
| 2007/0174014 | A1 | 7/2007 | Halm |
| 2007/0215801 | A1 | 9/2007 | Walsh et al. |
| 2008/0273171 | A1 | 11/2008 | Huth et al. |
| 2009/0201465 | A1 | 8/2009 | Huth |
| 2010/0253907 | A1 | 10/2010 | Korb et al. |
| 2010/0259723 | A1 | 10/2010 | Korb et al. |
| 2011/0199576 | A1 | 8/2011 | Huth et al. |
| 2011/0242482 | A1 | 10/2011 | Olsen |
| 2011/0273669 | A1 | 11/2011 | Abitbol et al. |
| 2012/0002169 | A1 | 1/2012 | Huth et al. |
| 2012/0105803 | A1 | 5/2012 | Huth et al. |
| 2013/0141698 | A1 | 6/2013 | Huth et al. |
| 2013/0169933 | A1 | 7/2013 | Wang |
| 2013/0208246 | A1 | 8/2013 | Huth et al. |
| 2013/0229624 | A1 | 9/2013 | Korb et al. |
| 2013/0293842 | A1 | 11/2013 | Grenon et al. |
| 2014/0104574 | A1 | 4/2014 | Grenon et al. |
| 2014/0118699 | A1 | 5/2014 | Huth et al. |
| 2015/0351626 | A1 | 12/2015 | Huth et al. |
| 2015/0351627 | A1 | 12/2015 | Huth et al. |
| 2015/0351628 | A1 | 12/2015 | Huth et al. |
| 2016/0345821 | A1 | 12/2016 | Huth et al. |
| 2017/0280991 | A1 | 10/2017 | Huth et al. |
| 2017/0280992 | A1 | 10/2017 | Huth et al. |

OTHER PUBLICATIONS

Examination Report for European Patent Application No. 15735765.8, dated Oct. 18, 2018, 4 pages.

International Search Report and Written Opinion for International Patent Application No. PCT/US2015/030392, dated Oct. 5, 2015, 12 pages.

International Preliminary Report on Patentability and Written Opinion for International Patent Application No. PCT/US2015/030392, dated Dec. 15, 2016, 12 pages.

Non-Final Office Action for U.S. Appl. No. 14/298,176, dated Jun. 29, 2016, 15 pages.

Final Office Action for U.S. Appl. No. 14/298,176, dated Dec. 23, 2016, 18 pages.

Applicant-Initiated Interview Summary for U.S. Appl. No. 14/298,176, dated Mar. 15, 2017, 3 pages.

Non-Final Office Action for U.S. Appl. No. 14/298,176, dated Apr. 4, 2017, 16 pages.

Final Office Action for U.S. Appl. No. 14/298,176, dated Oct. 20, 2017, 18 pages.

Advisory Action for U.S. Appl. No. 14/298,176, dated Jan. 16, 2018, 3 pages.

Non-Final Office Action for U.S. Appl. No. 14/298,176, dated Mar. 28, 2018, 18 pages.

Notice of Allowance for U.S. Appl. No. 14/298,176, dated Sep. 26, 2018, 8 pages.

Notice of Allowance for U.S. Appl. No. 14/298,176, dated Mar. 14, 2019, 8 pages.

Notice of Allowance for U.S. Appl. No. 14/831,678, dated Feb. 16, 2017, 9 pages.

Non-Final Office Action for U.S. Appl. No. 15/625,815, dated Jul. 2, 2018, 4 pages.

Notice of Allowance for U.S. Appl. No. 15/625,815, dated Mar. 20, 2019, 7 pages.

Notice of Allowance for U.S. Appl. No. 15/627,077, dated May 4, 2018, 7 pages.

Non-Final Rejection for U.S. Appl. No. 14/298,036, dated Nov. 2, 2015, 7 pages.

Notice of Allowance for U.S. Appl. No. 14/298,036, dated May 4, 2016, 7 pages.

Supplemental Notice of Allowance for U.S. Appl. No. 14/298,036, dated Aug. 17, 2016, 7 pages.

Non-Final Office Action for U.S. Appl. No. 15/172,083, dated Oct. 5, 2016, 5 pages.

Notice of Allowance for U.S. Appl. No. 15/172,083, dated Dec. 2, 2016, 7 pages.

Brennan, N.A. et al., "Clinical Application of the Oxygen Transmissibility of Powered Contact Lenses," Clinical and Experimental Optometry, 1991, vol. 74 (6), pp. 212.

Hecht, E. et al., "Interference" in: Optics, Chapter 9, Addison-Wesley Publishing Company, 2002, pp. 426-428.

Kwon, O. et al., "Rough Surface Interferometry at 10.6 Microm," Applied Optics, 1980, vol. 19 (11), 8 pages.

Lira M., et al., "The Effect of Lens Wear on Refractive Index of Conventional Hydrogel and Silicone-hydrogel Contact Lenses: A Comparative Study," Contact Lens & Anterior Eye, 2008, vol. 31 (2), pp. 89-94.

Pillai, H.P., et al., "Optical Modeling of a-Si:H Thin Film Solar Cells with Rough Interfaces", pp. 159-162.

Rakels, J.H., "Influence of the Surface Height Distribution on the Total integrated Scatter (TIS) Formula," Nanotechnology, 1996, vol. 7, pp. 43-46.

Zeman M., et al., "Optical Modeling of a-Si:H Solar Cells with Rough Interfaces: Effect of Back Contact and Interface Roughness," Journal of Applied Physics, 2000, vol. 88 ( 11 ), pp. 6436-6443.

International Search Report and Written Opinion for International Patent Application No. PCT/US2012/067188, dated Jul. 2, 2013, 11 pages.

Notice of Allowance for U.S. Appl. No. 13/310,026, dated Apr. 29, 2013, 9 pages.

Notice of Allowance for U.S. Appl. No. 13/310,026, dated Aug. 1, 2013, 9 pages.

Notice of Allowance for U.S. Appl. No. 14/058,564, dated Jun. 24, 2015, 9 pages.

Corrected Notice of Allowability for U.S. Appl. No. 14/058,564, dated Aug. 13, 2015, 5 pages.

International Preliminary Report on Patentability for International Patent Application No. PCT/US2012/067188, dated Jun. 12, 2014, 7 pages.

Atchison, et al., "Chromatic Dispersions of the Ocular Media of Human Eyes," Journal of the Optical Society of America, vol. 22, No. 1, Jan. 2005, pp. 29-37.

Behar-Cohen, F., et al., "Ultraviolet Damage to the Eye Revisited: Eye-Sun Protection Factor (E_SPF), a New Ultraviolet Protection Label for Eyewear," Clinical Opthalmology, vol. 8, Aug. 2014, pp. 87-104.

Bosch, S., et al., "A Method for the Measurement of Reflectances of Spherical Surfaces," Measurement Science and Technology, vol. 4, No. 2, 1993, pp. 190-192.

Fogt, N., et al., "Interferometric Measurement of Tear Film Thickness by Use of Spectral Oscillations," Journal of Optical Society of America, vol. 15, No. 1, 1998, pp. 268-275.

Gardner, et al., "Tear Film Thickness: Responsiveness to Potential Cognitive Demands," American Academy of Optometry, Tampa Dec. 2004, 1 page.

Geldis et al., "The Impact of Punctal Occulsion on Soft Contact Lens Wearing Comfort and the Tear Film," Eye and Contact Lens, vol. 34, No. 5, 2008, pp. 261-265.

Goto, E., et al., "Computer-Synthesis of an Interference Color Chart of Human Tear Lipid Layer, by a Colorimetric Approach," Investigative Opthalmology and Visual Science, vol. 44, No. 11, 2003, pp. 4693-4697.

Goto, E., et al., "Differentiation of Lipid Tear Deficiency Dry Eye by Kinetic Analysis of Tear Interference Images," Archives of Opthalmology, vol. 121, No. 2, 2003, pp. 173-180.

Hinel, E., et al., "Concurrent Interferometric Measures of Lipid Layer Thickness and Tear Film Thinning Before and After Application of Lipid Emulsion Drop," American Academy of Optometry, Anaheim, Oct. 2008, 1 page.

Kimball, et al., "Evaporation is the Primary Mechanism of Pre-Corneal Tear Film Thinning," Available online at: «http://www.aaopt.org/Submission/Search/SubmissionViewer.asp"SID=2»,
Acccessed Feb. 25, 2009.

(56) References Cited

OTHER PUBLICATIONS

Kimball, et al., "Improving Interferometric Tear Thickness Measurements by Using Longer Wavelengths," Available online at: «http://www.aaopt.org/Submission/Search/SubmissionViewer.asp"SID=7», Accessed Feb. 25, 2009.
King, S., et al., "Three Interferometric Methods for Measuring the Thickness of Layers of the Tear Film," Optometry and Vision Science, vol. 76, No. 1, 1999, pp. 19-32.
King, S., et al., "Why does Dry Eye Affect Inferior Cornea More than Superior Cornea," American Academy of Optometry, 2002, pp. 1-2.
King-Smith, P., et al., "In vivo Measurement of the Thickness of Human Corneal Endothelium and Descemets Membrane Using Interferomery. E-Abstract 157," Investigative Opthalmology and Visual Science, vol. 43, 2002.
King-Smith, P., et al., "Noninvasive Measurement of the Thickness of the Human Corneal Endothelium and Descamet's Membrane," American Academy of Optometry, Dec. 8, 2001, pp. 1-2.
King-Smith, P., et al., "Roughness of the Corneal Surface by Interferometry," Association for Research in Vision and Opthalmology, May 6, 2007, 1 page.
King-Smith, P., et al., "The Thickness of the Human Precorneal Tear Film. Evidence from Reflection Spectra," Investigative & Visual Science, vol. 41, No. 11, 2000, pp. 3348-3359.
King-Smith, P., et al., "The Thickness of the Tear Film," Current Eye Research, vol. 29, Nos. 4-5, Taylor & Francis Health Sciences, 2004, pp. 357-368.
King-Smith, P., et al., "Interferometric Analysis of Reflections from the Tear Film and Ocular Surface," Available online at: «http://www.aaopt.org/Submission/Search/SubmissionViewer.asp"SID=4», Accessed Feb. 25, 2009.
King-Smith, P., et al., "Measurement of the Thickness of the Lipid Layer of the Tear Film Using Reflection Spectra," Association for Research in Vision and Opthalmology, Inc., Grand Floridian A, Program 1540, 2008.
King-Smith, P., et al., "A Tear Layer of Thickness 1.6 to 7.3 Micrometer Determined from Reflectance Spectra," Investigative Opthalmology & Visual Science, vol. 39, No. 4, 1998, pp. 2446-B303.
King-Smith, P., et al., "Can the Mucus Layer of the Tear Film be Deomstrated by Interferometry," Investigative Opthalmology & Visual Science, vol. 45, 2004, pp. 1-2.
King-Smith, P., et al., "Further Evidence that the Thickness of the Normal Human Tear Film is about 3 Micrometre," Investigative Opthalmology & Visual Science, vol. 41, No. 4, 2000, pp. 337-B337.
King-Smith, P., et al., "Interferometric Imaging of the Full Thickness of the Precorneal Tear Film," Journal of the Optical Science of America A, Optics, Image Science, and Vision, vol. 23, No. 9, 2006, pp. 2097-2104.
King-Smith, P., et al., "Is the Thickness of the Tear Film About 40 Micrometre or About 3 Micrometre," Investigative Opthalmology & Visual Science, vol. 40, No. 4, 1999, pp. 2876-B751.
King-Smith, P., et al.,"Measurement of Tear Film Thickness by Spectro-Photometry," Investigative Opthalmology & Visual Science, vol. 37, No. 3, 1996, pp. 4984-B594.
King-Smith, P., et al., "Is Inferior Tear Film Thinner than Superior Tear Film," Investigative Opthalmology & Visual Science, vol. 44, 2003, p. 2476.
Korb, D.R., et al., "Tear Film Lipid Layer Thickness as a Function of Blinking," Cornea, vol. 13, No. 4, 1994, pp. 354-359.

Korb, D.R., et al., "The Effect of Two Novel Lubricant Eye Drops on Tear Film Lipid Layer Thickness in Subjects with Dry Eye Symptoms," Optometry and Vision Science, vol. 82, No. 7, 2005, pp. 494-601.
Nichols, J.J., et al., "Assessing Visual Parameters in Dry Eye Disease," Cornea and Contact Lens, Available online at: «http://www.aaopt.org/Submissions/Search/SubmissionViewer.asp"SID=2», Accessed Feb. 25, 2009.
Nichols, J.J., et al., "Lipid Layer Thickness and Tear Film Thinning Before and After Application of a Lipid Emulsion Drop," Association for Research in Vision and Opthalmology, 2008.
Nichols, J.J., et al., "Tear Film Thickness and Thinning Rate Following a Six-Week Trial of 2% Diquafosol Tetrasodium vs. Placebo in Dry Eye Patients," 2006.
Nichols, J.J., et al., "The Impact of Contact Lens Care Solutions on the Thickness of the Tear Film and Contact Lens," Cornea, Clinical Sciences, vol. 24, No. 7, 2005, pp. 825-832.
Nichols, J.J., et al., "Hydrogel Contact Lens Binding Induced by Contact Lens Rewetting Drops," Optometry and Vision Science, vol. 85, No. 4, 2008, pp. 236-240.
Nichols, J.J., et al., "Thickness of the Pre-and Post-Contact Lens Tear Film Measured In Vivo by Interferometry," Investigative Opthalmology & Visual Science, vol. 44, No. 1, 2003, pp. 68-77.
Nichols, J.J., et al., "Thinning Rate of the Precorneal and Prelens Tear Films," Investigative Opthalmology & Visual Science, vol. 46, No. 7, 2005, pp. 2353-2361.
Nicols, et al., "Role of Lipid Layer as a Barrier to Pre-Lens Tear Film Thinning," American Academy of Optometry, Anaheim, Oct. 25, 2008, 1 page.
Scaffidi, R.C., et al., "Comparision of the Efficacy of Two Lipid Emulsion Eyedrops in Increasing Tear Film Lipid Layer Thickness," Eye Contact Lens, vol. 33, No. 1, 2007, pp. 38-44.
Schlote, T., et al., "Marked Reduction and Distinct Patterns of Eye Blinking in Patients with Moderately Dry Eyes During Video Display Terminal Use," Graefe's Archive for Clinical and Experimental Opthalmology, vol. 242, No. 4, 2004, pp. 306-312.
"Schott BK7 Refractive Index Reference, Which Is Equivalent to and Replaces Schott Technical Information Document TIE-29," Available online at: «http://ltiw3.iams.sinica.edu.tw/support/OpticsGuide/chap04_Material_Properties.pdf», 2005, 17 pages.
Stenzel, O., "The Physica of Thin Fim Optical Spectra: An Introduction," in: Springer Series in Surface Sciences, vol. 44, ERTL G., Eds., Springer-Verlag Berin Heidelberg, 2005, pp. 71-98.
Tiffany, J.M., et al., "Refractive index of Meibomian and Other Lipids," Current Eye Research, vol. 5, No. 11, 1986, pp. 887-889.
Yap, M., "Tear Break-Up Time is Related to Blink Frequency," Acta Opthalmologica, vol. 69, No. 1, 1991, pp. 92-94.
Zhu, H., et al., "A Mathematical Model for Ocular Tear and Solute Balance," Current Eye Resesarch, vol. 30, No. 10, 2005, pp. 841-854.
International Search Report for International Patent Application No. PCT/US2008/062682, dated Nov. 5, 2008, 6 pages.
International Preliminary Report on Patentability and Written Opinion for International Patent Application No. PCT/US2008/062682, dated Nov. 10, 2009, 12 pages.
Examination Report No. 1 for Australian Patent Application No. 2015268808, dated May 3, 2019, 3 pages.
International Search Report for International Patent Application No. PCT/US2015/030385, dated Jul. 27, 2015, 3 pages.
International Preliminary Report on Patentability and Written Opinion for International Patent Application No. PCT/US2015/030385, dated Dec. 15, 2016, 12 pages.
Examination Report No. 1 for Australian Patent Application No. 2015268810, dated May 3, 2019, 3 pages.

FAST ABSOLUTE-REFLECTANCE METHOD FOR THE DETERMINATION OF TEAR FILM LIPID LAYER THICKNESS

CROSS-REFERENCE TO RELATED APPLICATIONS

The present application is a continuation of U.S. patent application Ser. No. 14/298,176 to Huth and Tran, "Fast Absolute-Reflectance Method for the Determination of Tear Film Lipid Layer Thickness," filed Jun. 6, 2014, now issued as U.S. Pat. No. 10,368,738, which is incorporated herein by reference in its entirety.

The present application is related to U.S. patent application no. 14/298,036 to Huth and Tran, "Method for Rapid Calculation of Tear Film Lipid and Aqueous Layer Thickness and Ocular Surface Refractive Index from Interferometry Spectra," filed Jun. 6, 2014, now issued as U.S. Pat. No. 9,456,741, which is incorporated herein by reference in its entirety.

BACKGROUND

The present invention relates to determination of tear film lipid layer thickness.

Dry eye disease is most often caused by excessive tear film evaporation, leading to hyperosmolarity of the tear film, resulting in ocular surface inflammation and exacerbation of the problem. Excessive tear film evaporation is often caused by an abnormal tear film lipid layer, either in amount or in quality. The amount or quality of tear film lipid can manifest itself in changes in thickness of the lipid layer. Generally, a thicker lipid layer is associated with a normal tear film, whereas the opposite is often the case for dry eye. Present clinical measurements of the tear film lipid layer are for the most part qualitative or semi-quantitative in nature. Korb, in U.S. Pat. Nos. 8,591,033 and 8,585,204, disclose a quantitative method for measuring the thickness of the tear film lipid layer. However, this method does not measure the lipid layer over the central cornea where tear film thinning and breakup due to evaporation is maximal and where it is believed a better diagnosis of dry eye can be obtained. Huth, in U.S. Pat. No. 8,602,557 B2 (incorporated herein by reference in its entirety) also disclose a quantitative method for measuring the thickness of the tear film lipid layer as part of a method to simultaneously measure the tear film aqueous layer and the corneal surface refractive index. However, this method requires as long as 475 seconds to complete the calculations for a single tear film spectrum.

SUMMARY

Thus, it is the object of the present invention to overcome the limitations of the prior art, and to increase the sensitivity, accuracy and precision of the measurement of the tear film lipid layer. Fast, accurate and precise lipid layer thickness-determination methods are also needed for the quantitative evaluation of the effects of novel dual-function lipid-supplementation tear formulas on the tear film lipid layer. Such methods are also needed to evaluate the effects of other eye drops, ophthalmic dry eye drugs and MPS solutions, and contact lenses on the tear film lipid layer.

In one embodiment, the invention provides a method of determining tear film lipid layer thickness. The method includes the steps of measuring a tear film aqueous plus lipid layer relative reflectance spectrum using a wavelength-dependent optical interferometer; converting the measured tear film aqueous plus lipid layer relative reflectance spectrum to a calculated absolute reflectance spectrum; and comparing the calculated absolute reflectance spectrum to a theoretical absolute lipid reflectance spectrum to determine a tear film lipid layer thickness.

In another embodiment the invention provides a system for determining tear film lipid layer thickness. The system includes a wavelength-dependent optical interferometer and a controller. The controller is in communication with the interferometer and is configured to measure a tear film aqueous plus lipid layer relative reflectance spectrum using the interferometer, convert the measured tear film aqueous plus lipid layer relative reflectance spectrum to a calculated absolute reflectance spectrum, and compare the calculated absolute reflectance spectrum to a theoretical absolute lipid reflectance spectrum to determine a tear film lipid layer thickness.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Human tear film lipid layer thickness is believed to be between 20-200 nm. Central corneal tear film lipid layer thickness rarely exceeds about 120 nm, however, and also can be less than 20 nm in thickness. Normal wavelength-dependent optical interferometric methods for the determination of thin film thickness, based upon the analysis of the increasing number of cosine-function spectral oscillations with thickness, are unsuitable for this range. This is so because even at 200 nm thickness, only half an oscillation is visible within the 575-1075 nm spectral wavelength range of the typical optical interferometer (FIG. 1).

Figure 1:
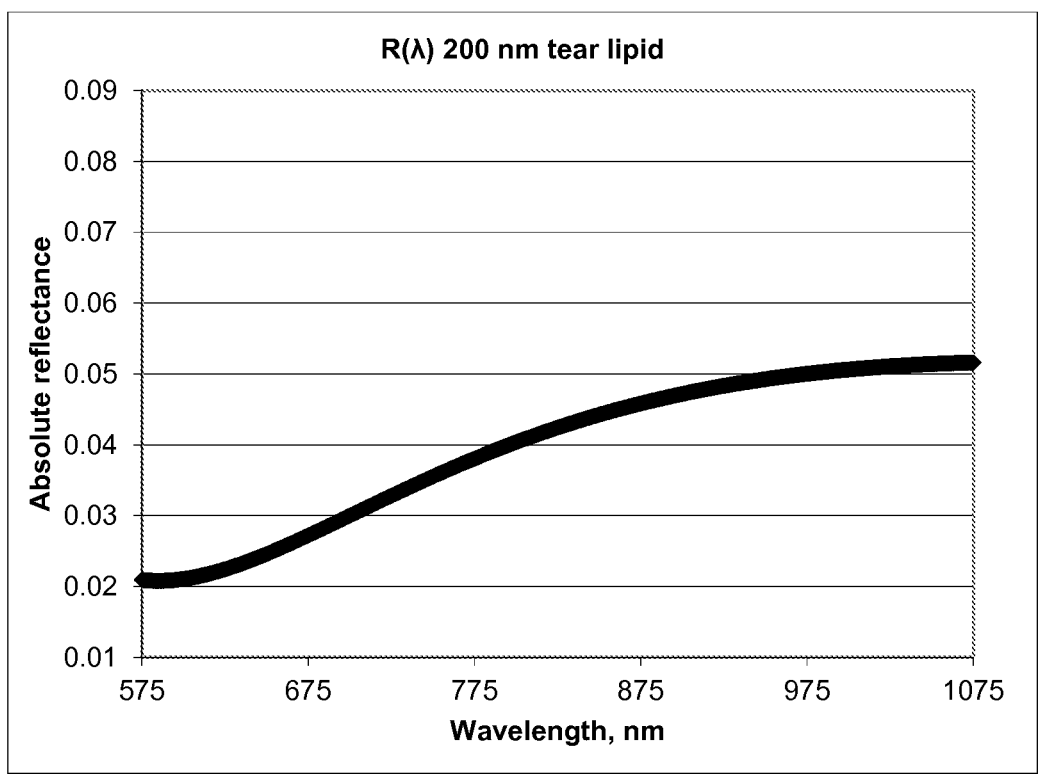
FIG. 1 shows absolute reflectance for a 200 nm tear lipid film layer measured in a wavelength range of 575 nm to 1075 nm.

Accordingly, the answer to this problem is to base the thicknesses upon absolute optical reflectivity, also illustrated in FIG. 1, where absolute reflectivity of a 200 nm lipid layer is 0.02=2% at 575 nm. Thus, one needs to compare the absolute reflectivity spectrum of a tear lipid layer to a standard reflectivity spectrum such as seen in FIG. 1. The approach to achieving this is disclosed herein.

Interferometry measurements are typically determined as relative percent light reflection values, where the measurements from a subject's tear film and cornea are expressed relative to measurements obtained from a reference material (e.g. a particular glass material having a radius of curvature comparable to that of a cornea, e.g. ranging from 7-9 mm, in particular 7.75 mm). The ratio of the light reflectance from the subject's tear film and cornea, $R(\lambda)$ sample, to the light reflectance from the reference, $R(\lambda)$ reference, is multiplied by 100 by typical spectrometer and CCD detector software, so that the final relative light reflection values are expressed as percentages; the percentage values are determined for a range of wavelengths to obtain a spectrum. Thus, the y-axis of a measured spectrum corresponds to $100 \times R(\lambda)$ sample/$R(\lambda)$ reference.

As an initial step in the development of the methods of the present invention, the theoretical absolute spectra for lipid layers of various thicknesses were calculated. Given that these theoretical absolute spectra have similar shapes or slopes to one another, but different absolute optical reflectivity at different wavelengths, correlating the theoretical absolute spectra with observed spectra requires determining the absolute reflectance spectrum from the measured data and correlating the absolute spectra with the theoretical spectra. Experimentation is required, however, to account for discrepancies between theoretical predicted spectra and actual measured spectra. Lipid layer standards of known thicknesses are not available and so it is not possible to perform calibrations using lipids. Instead, a series of calibrations was performed using commercially-available standards having layers of silicon dioxide of known thicknesses, comparable to thicknesses of tear film lipid layers. The measured spectra for the silicon dioxide standards were compared to the predicted theoretical absolute spectra for silicon dioxide layers of the same thicknesses and a correction algorithm was produced which can be used to obtain the absolute reflectance values for measured tear film lipid layers. The correction algorithm accounts for changes in light reflection arising from the geometry of a curved reference lens or from non-orthogonal placement of a flat reference surface with respect to incident light and from out-of-focus light reflection.

In various embodiments, the disclosed methods are modifications of a procedure for calculation of absolute reflectance of the presumed tear structure, involving an air interface with a single lipid layer overlying an aqueous layer.

In the aforementioned procedure, $n_0$, $n_1$, and $n_2$ are the refractive indices of the air, lipid layer, and aqueous layer, respectively, for which fixed values of $n_0=1$, $n_1=1.48$, and $n_2=1.33$ have been used. In one embodiment of the present invention, the respective complex refractive indices are used for $n_1$ and $n_2$, each of which changes with wavelength.

The Fresnel indices of reflection $r_1$ and $r_2$ for the air-lipid and lipid-aqueous interfaces are, respectively:

$$r_1=(n_0-n_1)/(n_0+n_1) \text{ and } r_2=(n_1-n_2)/(n_1+n_2)$$

Since energy is proportional to the square of amplitude, $R(\lambda)=R \times R^*=|R^2|$, where $R^*$ is the conjugate complex numbers of R. Thus, from Euler's equation:

$$R(\lambda)=(r_1^2+r_2^2+2r_1r_2 \cos 2\delta_1)/(1r_1^2r_2^2+2r_1^2 \cos 2\delta_1)=1-(8n_0n_1^2n_2)/((n_0^2+n_1^2)(n_1^2+n_2^2)+4n_0n_1^2n_2+(n_0^2-n_1^2)(n_1^2-n_2^2)\cos 2\delta_1)$$

where a phase difference between two waves $r_1$ and $r_2$, is $2\delta_1$ and $$2\delta_1=(4\pi/\lambda)n_1 d \cos\varphi_1$$

where $\varphi_1$ is the angle of refraction of the incident light upon the lipid layer,
which=9.369° for the wavelength-dependent optical interferometer used in the methods of the present invention, thus $\cos \varphi_1=0.986659$.

The complex refractive indices for $n_1$ (lipid) and $n_2$ (aqueous) are used:

$$n_1=$$

$$nd=y=\text{sqrt}(1+(((-851.03)*x*x)/(x*x-(816.139)))+\\ (((420.267)*x*x)/(x*x-(-706.86))))$$

plus $((((431.856)*x*x)/(x*x-2355.29))))$ where x=wavelength and where nd=Sellmeier equation form of tear meibomian lipid refractive index derived from primary refractive index data from Tiffany, J M. Refractive index of meibomian and other lipids. *Current Eye Research.* 5(11), 1986; 887-889: 430 nm: nd=1.5126; 450 nm:1.5044; 510 nm: 1.4894; 590 nm:1.4769; 710 nm:1.4658. The Sellmeier equation coefficients were derived by fitting the limited Tiffany data (no data exist beyond 710 nm, where most of the spectral range of the interferometer exists (spectral range: 559-1085 nm)) first to a polynomial (nd=5.04e−7 x2−0.00736x+1.73481, wherein x=wavelength) to generate forecasted refractive index values at 600, 620, 640 and 680 nm, followed by fitting the Tiffany+forecasted refractive index data set to the Sellmeier equation format wherein refractive index data beyond 710 nm could be calculated and utilized. The Sellmeier equation format for lipid refractive index data is believed to provide more accurate refractive index information, which is critical for accurate lipid layer thickness calculations.

$$n_2=1.32806+0.00306*(1000/\lambda)^2$$

Figure 2:
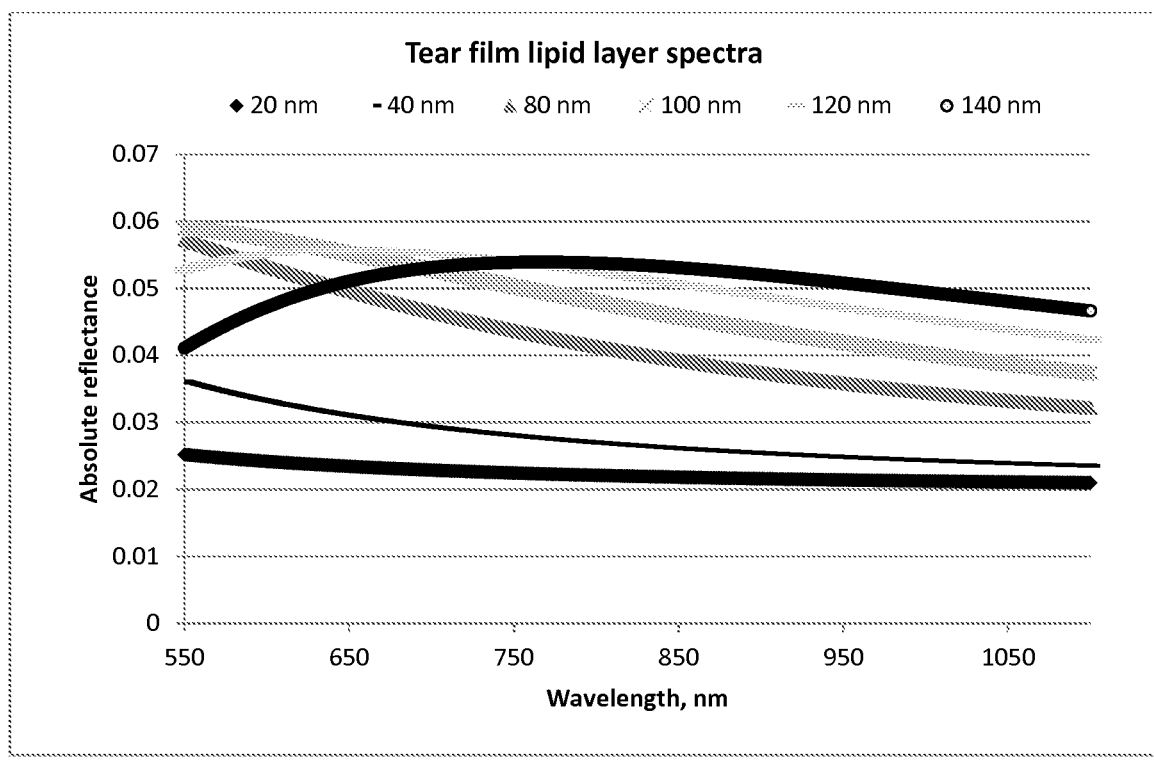
FIG. 2 shows calculated absolute reflectance spectra for lipid layers thicknesses in a range of 0-140 nm.

Using the above equations, an Excel spreadsheet is created in which the values of the three refractive indices $n_0$, $n_1$ and $n_2$ are calculated (except for $n_0$, which is always 1) for the wavelengths within the wavelength range measured by the interferometer (e.g., for wavelengths between 559-1085 nm). Then, using the expanded Euler's equation with all terms, $R(\lambda)$ is calculated for a series of lipid layer thicknesses, d. The results from 575-1075 nm are seen in FIG. 2, presenting a series of absolute-value reflectance spectra for lipid layers of various thicknesses.

The spectrum (not shown) for a lipid layer of 0 nm thickness is very flat, lies just below that of a 20 nm thick lipid layer and produces an absolute reflectance of 0.02% of the incident light at 550 nm. It can be seen in FIG. 2 that there is little difference in the slopes of the lipid layer spectra between 20-100 nm thicknesses, further reinforcing the need to base lipid layer thickness calculations upon absolute reflectance values rather than parameters such as the slope or shape of the spectra. Thus, a 20 nm lipid layer will reflect about 0.025=2.5% of the incident light at 550 nm, whereas a 100 nm lipid layer will reflect about 0.06=6% of the incident light at 550 nm. At 120 nm thickness and larger, the slope of absolute reflectance begins to change from a negative slope to a flat slope. Beyond 140 nm thickness, as seen in FIG. 1 for a 200 nm thickness, the slope becomes positive. Slope evaluation at 120 nm and beyond becomes a valuable tool to distinguish between a thin or thick lipid layer.

Figure 3:
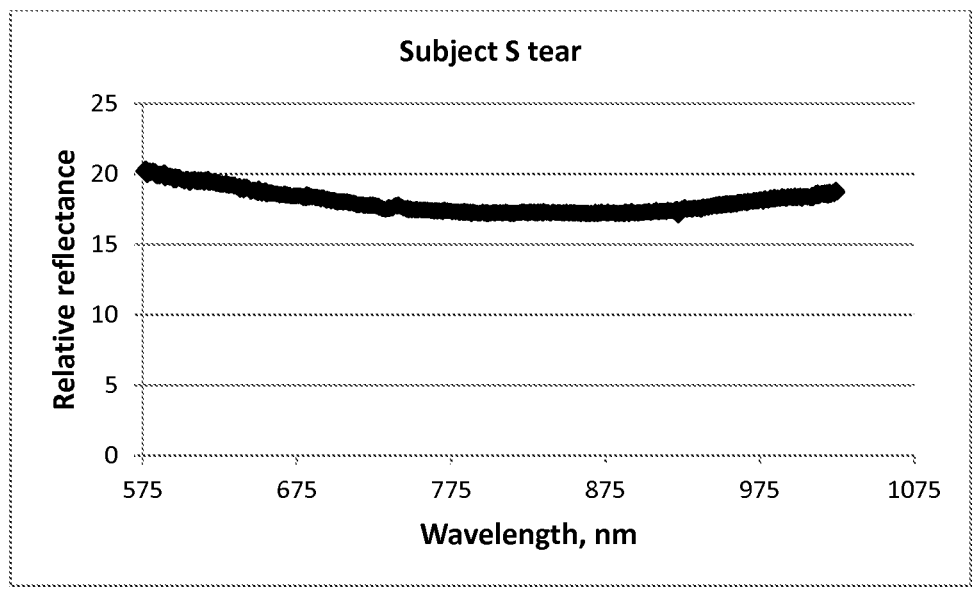
FIG. 3 shows an unmodified tear film lipid spectrum obtained using an interferometer.

Thus, for the majority of tear film lipid layers between 0-100 nm thickness, it is not a simple exercise to measure a tear lipid spectrum with a wavelength-dependent optical interferometer and compare it to one of the above absolute reflectance spectra. This is illustrated in FIG. 3, which shows an unmodified measured tear lipid spectrum.

Accordingly, each measured spectrum must be converted to a calculated absolute spectrum and then compared to the absolute reflectivity derived from theory. This comparison must be accomplished mathematically.

This new procedure required development and validation with thin film standards. Since thin lipid film standards are not available, thin $SiO_2$ film standards, produced via vapor deposition of $SiO_2$ onto pure flat Silicon wafer substrates were used. These standards are commercially available (VLSI Standards, Inc. San Jose, Calif. 95134-2006) and calibrated to within 0.1-0.01 nm thickness by NIST. The following $SiO_2$ standards were employed (the 0 nm standard was a pure silicon wafer without $SiO_2$; Table 1).

TABLE 1

| $SiO_2$ Actual thickness, nm |
|---|
| 0 |
| 48.26 |
| 95.01 |
| 188.58 |

Absolute reflectivity of these $SiO_2$ films were calculated, using the same procedure with the expanded Euler equation above, substituting the complex refractive indices below for $n_1$ and $n_2$ ($n_0$=air=1, as before).

$$SiO_2 n_1 = -9.3683E-11x^3 + 2.5230E-07x^2 - 2.3810E-04x + 1.5302E+00$$

$$Si\ n_2 = SQRT(1+((5.66474*\lambda*\lambda/((\lambda*\lambda)-119153))+ ((5.29869\lambda*\lambda*)\lambda*\lambda-(51556.1))) + ((-24642*\lambda*\lambda/((\lambda*\lambda)-(-146300000000)))))$$ (conversion of raw $n_2$ data to the Sellmeier equation form)

Figure 4:
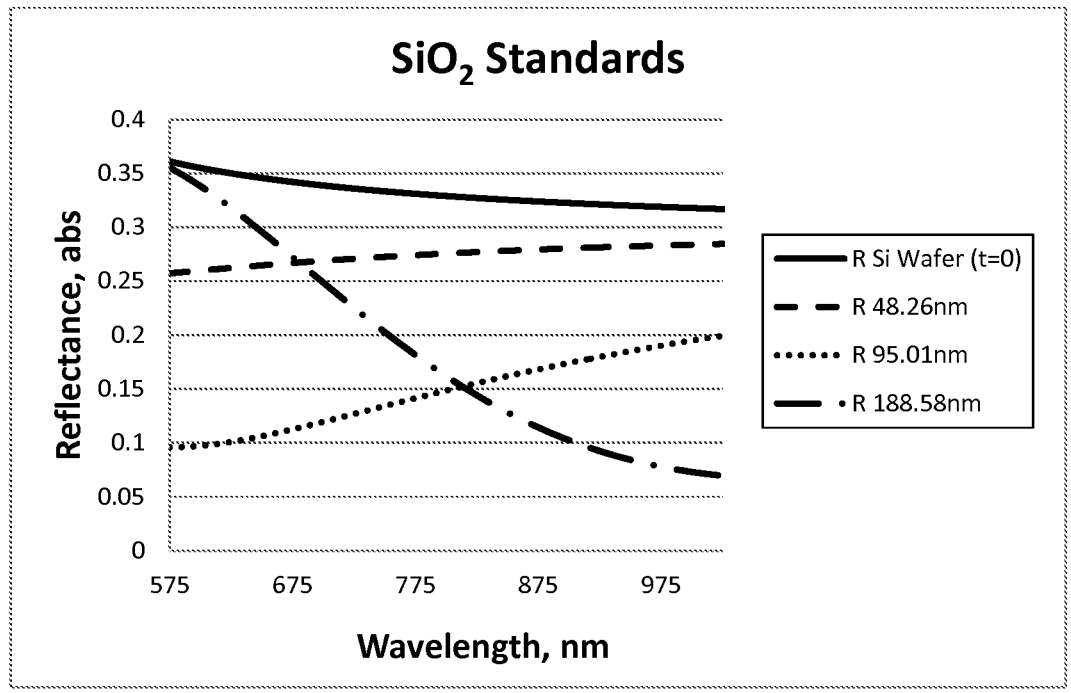
FIG. 4 shows absolute reflectance spectra for $SiO_2$ layers having thicknesses from 0 -188.6 nm.

The latter equation for the refractive index of pure silicon is in the form of the Sellmeier equation. This equation form is considered to provide very accurate values of the refractive index as a function of wavelength. Not all refractive index data are provided in this form, however. The resulting absolute reflectance spectra are seen in FIG. 4.

Interferometer-measured spectra for $SiO_2$ standards, as for measured tear film lipid spectra, are expressed as relative % reflectance, since the measured reflectance from a thin film is measured relative to the measured reflectance from a reference. The y-axis of a measured spectrum corresponds to 100×R($\lambda$) meas. sample/R($\lambda$) meas. reference.

A number of different references can be used, although the best reference for tear film spectra is one with the same radius of curvature as the cornea (r=7.75 mm), to allow for the same reflectance geometry. In certain embodiments, a spherically-curved BK7 glass reference lens is used for this purpose. A pure flat silicon wafer can also be used as the reference for the $SiO_2$ standards, since both surfaces are flat. The conversion procedure to convert a measured $SiO_2$ or tear film spectrum to a calculated absolute reflectance spectrum is to first divide by 100 and then to multiply the (R($\lambda$) meas. Sample/R($\lambda$) meas. Reference)×R($\lambda$) absolute reference. Here, R($\lambda$)absolute reference is the calculated theoretical reflectivity of the reference and the abbreviation for absolute when used throughout this disclosure will be: abs. This result can then be compared mathematically to a theoretical SiO2 or tear lipid spectrum, as illustrated in FIG. 4 for $SiO_2$. In order to accomplish this procedure, one has to first calculate R($\lambda$) absolute reference (for pure Silicon or BK7). The equation which is used is derived from the following equations.

If incident light is unpolarized, and since R=|r|$^2$ (since reflected intensity is proportional to the square of the modulus of the electric field amplitude and the dielectric function), then total R=$(r_s+r_p)^2/2$.

Also, from Snell's law, where $\sin\psi=(n_1/n_2)\sin\varphi$, $\cos\psi = (1-(n_1^2/n_2^2)\sin^2\varphi)^{1/2}$.

Then, from the theory of interface reflection between two isotropic materials (e.g. air and an isotropic solid such as Si or BK7), the indices of reflection are determined as follows:

$$r_s=(n_1 \cos\varphi - n_2 \cos\psi)/(n_1 \cos\varphi + n_2 \cos\psi)=$$

$$(n_1 \cos\varphi - n_2(1-(n_1^2/n_2^2)\sin^2\varphi)^{1/2})/(n_1 \cos\varphi + n_2(1-(n_1^2/n_2^2)\sin^2\varphi)^{1/2}),\ and$$

$$r_P=(n_2 \cos\varphi - n_1 \cos\psi)/(n_2 \cos\varphi + n_1 \cos\psi)=$$

$$(n_2 \cos\varphi - n_1(1-(n_1^2/n_2^2)\sin^2\varphi)^{1/2})/(n_2 \cos\varphi + n_1(1-(n_1^2/n_2^2)\sin^2\varphi)^{1/2})$$

These equations may also be written as:

$$r_s=(n_1 \cos\varphi - (n_2^2-n_1^2\sin^2\varphi)^{1/2})/(n_1 \cos\varphi + (n_2^2-n_1^2\sin^2\varphi)^{1/2}),$$

since $(n_2^2-n_1^2\sin^2\varphi)^{1/2} = ((n_2((n_2^2/n_2^2)-(n_1^2/n_2^2)/\sin^2\varphi)^{1/2} = n_2(1-(n_1^2/n_2^2)\sin^2\varphi)^{1/2}$ and $$r_P=(n_2 \cos\varphi - n_1(1-(n_1^2/n_2^2)\sin^2\varphi)_{1/2})/(n_2\varphi + n_1(1-(n_1^2/n_2^2)\sin^2\varphi)^{1/2})$$

Then, since $n_1$=air=1, the equations above can be combined using the relationship R abs=$(r_s+r_p)^2/2$=R($\lambda$) abs Si or R($\lambda$) abs BK7 (i.e. to obtain calculated absolute reflectance values for silicon or BK7 glass):

$$R(\lambda)\ abs\ Si = (((0.986659 - D3*SQRT(1-(0.162799/D3)^2))/(0.986659 + D3*SQRT(1-(0.162799/D3)^2 + (((SQRT(1-(0.162799/D3)^2))-D3*0.986659)/((SQRT(1-(0.162799/D3)^2))+D3*0.986659))^2)/2$$

where D3=Sellmeier refractive index for Si at each $\lambda$, and where 0.986659=cos $\varphi$ and 0.162799=sin$\varphi$ and where each wavelength is an exact wavelength measured by the interferometer.

R($\lambda$) abs BK7 is calculated for each wavelength using the same equation, except D332 Sellmeier refractive index for BK7 at each $\lambda$.

Sellmeier BK7 n=SQRT(1+(1.03961212*G3*G3)/(G3*G3−0.00600069867)+(0.231792344*G3*G3)/(G3*G3−0.0200179144)+(1.01046945*G3*G3)/(G3*G3−103.560653)) where G3=interferometer wavelength in microns (BK7 refractive index ref=Schott technical information document TIE-29 (2005)).

Figure 5:
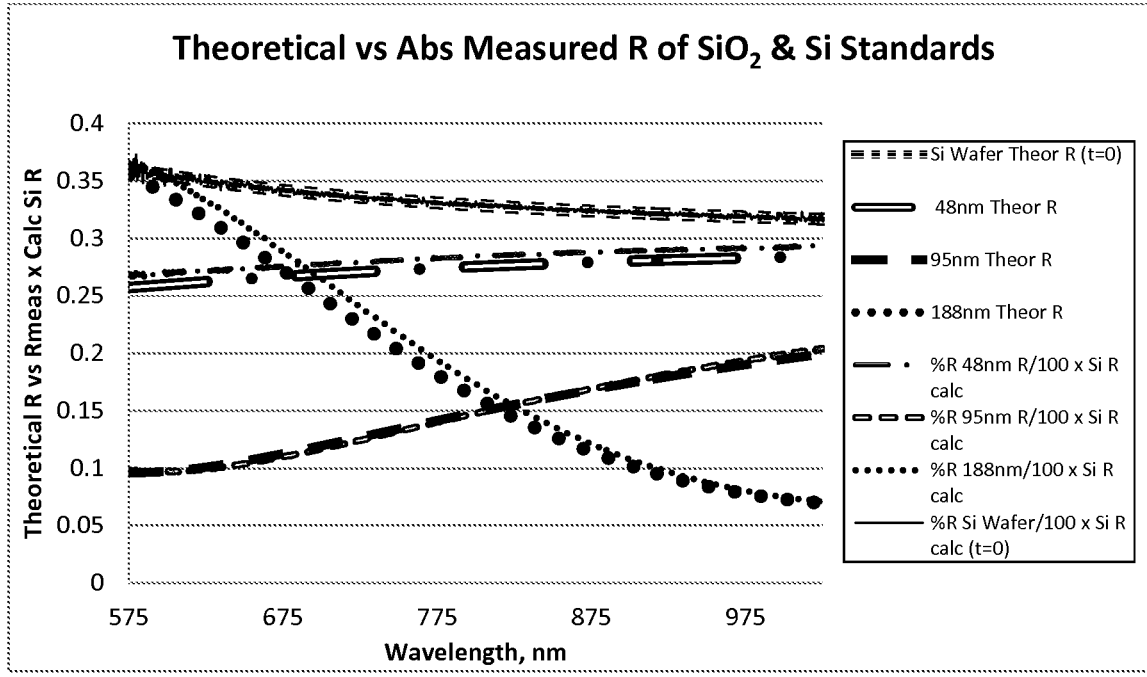
FIG. 5 shows the results of converting measured relative $SiO_2$ spectra to calculated absolute reflectance spectra, where each absolute reflectance spectrum obtained from measured data is compared to an equivalent calculated theoretical spectrum.

FIG. 5 shows the results of converting measured $SiO_2$ spectra (using a 4V or 4.5V light source voltage, 20 msec single scan) to calculated absolute reflectance spectra for various silicon reference standards. The measured relative spectra are first divided by 100 and then multiplied times R(λ) abs Si reference (Si abs R calculated) to obtain R(λ) abs $SiO_2$ sample spectra.

It can be seen that there are some relatively small differences between the theoretical and calculated absolute spectra. These differences can be mathematically calculated using an algorithm which compares the calculated absolute spectra to theoretical absolute spectra of various $SiO_2$ films of varying thicknesses. In one particular embodiment, this is accomplished by creating a Statistica software program (StatSoft®, Tulsa, Okla.) based upon the expanded Euler equation from above:

$$V5=(1-(8*v1*v2**2*v3)/((v12+v22*(v22+v32)+4*v1*v2**2*v3+((v12-v22)*(v22-v32)*(cos((4*3.14159*v2*a*0.98666/v4)))))$$

where
v5=R(λ) $SiO_2$ measured sample ×R(λ) abs Si reference (Si abs R calculated)/100
and where
v1=$n_0$ air=1,
v2=$n_1$(λ) $SiO_2$,
v3=$n_2$ (λ) Si,
v4=measured λ, and
the variable a, the fitted film thickness.

As shown below, the wavelength range for $SiO_2$ thin film standards must be limited to 575-1025 nm, to avoid signal weakness/potential optical aberration at the wavelength extremes. Thus, the program requires the input of five columns of calculated and measured data input as variables (i.e. v1-v5). The Non-linear Estimation method within the Statistica software is used, wherein the equation for v5 above is input as the function to be estimated into the space provided in the user specified regression, least squares module. The Statistica software program uses the Levenburg-Marquardt algorithm to achieve a minimum in the sum of squares of the differences between theoretical R and the product of R(λ) $SiO_2$ measured sample x R(λ) abs Si reference (Si abs R calculated)/100 at each wavelength. In various embodiments, other mathematical algorithms for fitting data are available within Statistica and other software platforms and can also be employed. This software module requires the number of calculation/fitting iterations to be selected. In one embodiment, fifty iterations were found to be acceptable, although other lower or higher numbers of iterations are also acceptable and can be readily determined by an evaluation of the p-level of the fit. All p-levels for thin films were found to be 0.00 and are thus highly significant.

The program also requires a starting value for the variable a-term, the fitted film thickness. This is indicated in the column labeled "STAT Input" in Table 2 below for the $SiO_2$ thin film standards. It was discovered through experiments with tear film spectra, presented below, that a starting value for the a-term that is too far from the actual thin film thickness value may converge to an incorrect result. It is believed that this may be a result of convergence to a local minimum in the least squares sum. Considerable time may be required to run the program multiple times with different starting values until the correct value is found. Moreover, the correct tear film lipid layer thickness is not known prior to calculation and thus the correct starting value is not known. Thus, selecting the proper starting value is important not only for a fast method, but also to achieve correct results. The human tear film lipid layer thickness typically ranges between 0 and 120 nm in thickness. Thus, in one particular embodiment a starting value of 65 nm has been determined to produce correct results for tear film lipid layer thickness between 0 and about 100 nm thickness as well as for $SiO_2$ thin film standards between 0 and 95 nm. Other starting values may be employed where necessary in cases where a 65 nm starting value is incorrect, as is the case for the 188.58 nm $SiO_2$ thin film standard, in which case a 200 nm starting value was used.

Subsequently, the validity of the method was demonstrated using a curved BK7 glass reference lens having an identical radius of curvature as the human cornea, 7.75 mm. This particular lens is used as a reference when making measurements of the human tear film in order to achieve optics as close as possible to those during the human tear film measurements.

Figure 6:
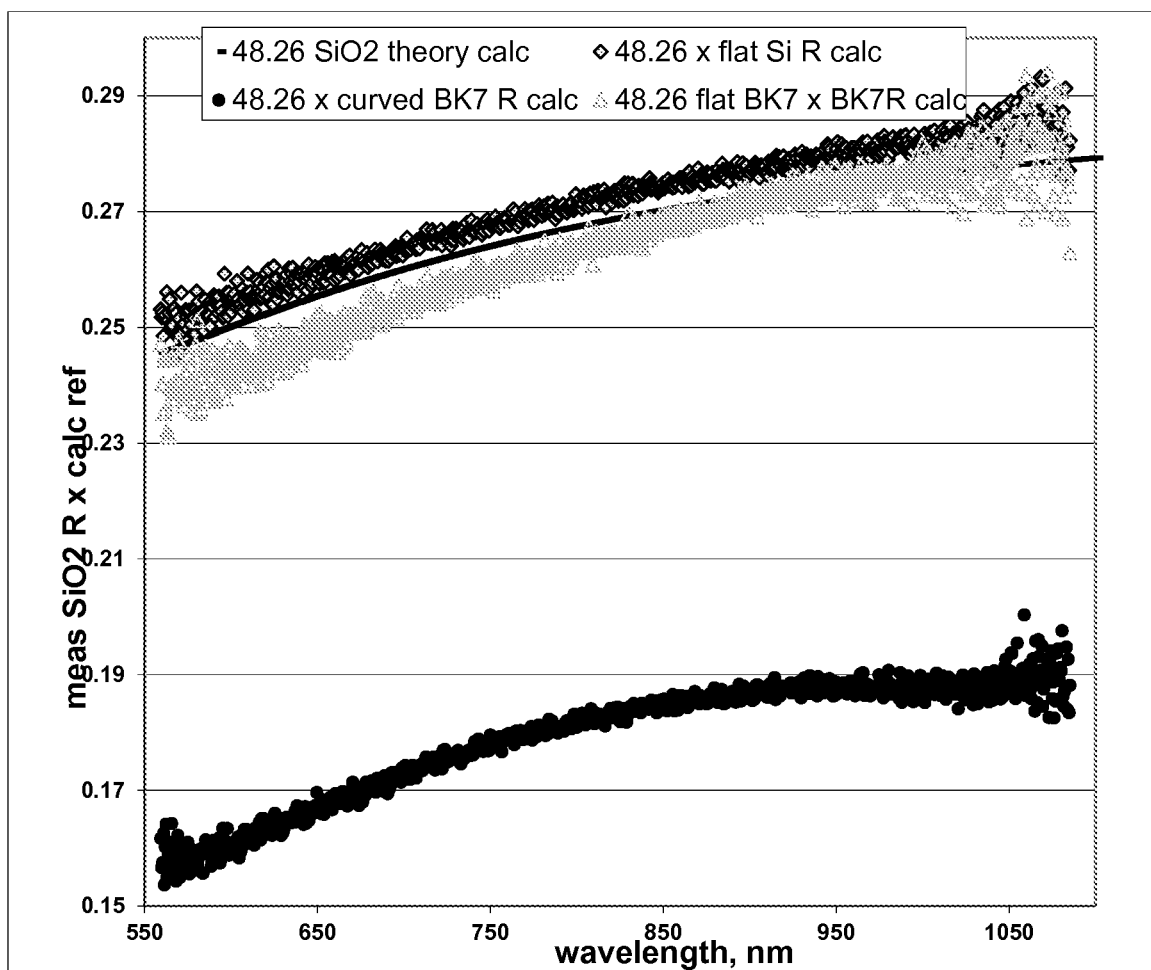
FIG. 6 shows the comparison between a calculated theoretical spectrum for a 48.26 nm SiO2 thin film standard compared to calculated absolute reflectance spectra obtained by converting measurements of the relative reflectance spectra for the 48.26 nm $SiO_2$ thin film standard which were measured relative to various reference materials, including a flat silicon wafer, a flat BK7 glass plate, and a curved BK7 glass lens having an identical radius of curvature as the human cornea, i.e. 7.75 mm.

A similar mathematical process was completed using measured $SiO_2$ thin film standard spectra with different reference materials. FIG. 6 shows absolute reflectance spectra obtained by converting measurements of the relative reflectance spectra for the 48.26 nm $SiO_2$ thin film standard which were measured relative to various reference materials, including a flat silicon wafer, a flat BK7 glass plate, and a curved BK7 glass lens having an identical radius of curvature as the human cornea, i.e. 7.75 mm. The absolute spectra, determined from measured relative spectra, are graphed relative to the calculated absolute spectrum for a 48.26 nm $SiO_2$ thin film. FIG. 6 shows that when either a flat Silicon wafer or flat BK7 reference lens is used instead of the curved BK7 lens, the spectra determined from the measured relative reflectance spectra closely match the respective theoretical spectrum. However, when the curved BK7 glass lens was used as the reference, the absolute reflectance spectrum that was obtained does not overlay the theoretical spectrum and instead is shifted downward. Without being limited as to theory, this is likely because the geometry of light reflection from the flat 48.26 nm $SiO_2$ and the flat BK7 standards is not the same as the light reflection from the curved BK7 glass lens.

Similar results were obtained with the other $SiO_2$ thin film standards (not shown). What became evident is that a final multiplier term (b) is required. The measured spectra must be multiplied by the b-term to match the theoretical spectra. Moreover, the b-term is a variable which changes between measured spectra. The b-term is in essence a light focusing term and corrects for non-identical focusing between the reference lens measurement and the human tear film measurement. Thus, the expanded Euler equation becomes:

$$V5=(1-(8*v1*v2**2*v3)/((v12+v22*(v22+v32)+4*v1*v2**2*v3+((v12-v22)*(v22-v32)*(cos((4*3.14159*v2*a*0.98666/v4)))))*b$$

where
v5=R(λ) $SiO_2$ measured sample x R(λ) abs Si reference (Si abs R calculated)/100
and where
v1=$n_0$ air=1,
v2=$n_1$(λ) $SiO_2$,
v3=$n_2$ (λ) Si,
v4=measured λ, and the variable a, the fitted film thickness, and the variable b, the final correction term which moves the measured spectrum up or down on the theoretical R axis (y-axis) to achieve a match with theory.

In one embodiment, the software program requires the b-term to be on the right-hand side of the equation and at the end of the equation, since it requires starting input values for any variables (here a and b) to be in the same order (left to right) in which they appear in the equation program line and the variable input value program line. Since the right side of the above equation is the calculated theoretical reflectance which iteratively matches the calculated measured absolute reflectance on the left hand side, the b-term may have a value less than 1 (a b-term on the right side of 0.5 would be equivalent to a b-term on the left side of 2.0). It was determined through experiments varying the starting value of the b-term from 0 to 1.30 that the b-term value can start at a relatively wide range of values, for example between 0.40-0.80 or between 0 and 1.30, so that the program achieves the correct thickness. The center of the b-term range is about 0.66 and thus this is a good starting value.

All scan times herein for the $SiO_2$ thin film standards are single 20 msec scans, whereas tear film spectra are typically sums of twelve 21 msec scans. The program is very fast, calculating results for a single spectrum in under a second and results for 50 spectra in 11 seconds. The results for the $SiO_2$ thin film standards are shown in Table 2 below.

Figure 7:
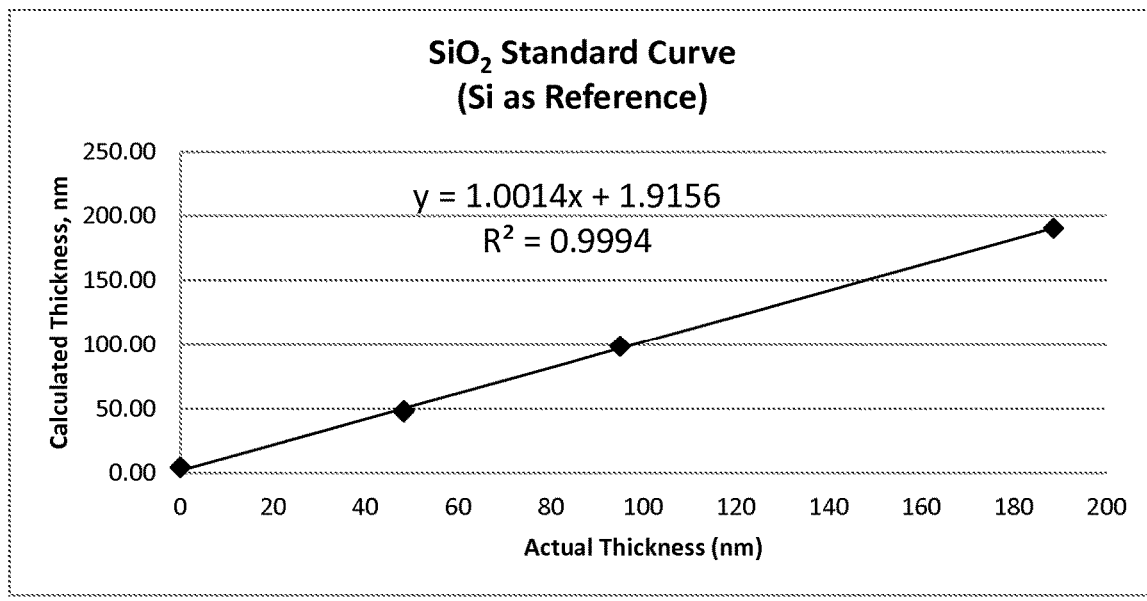
FIG. 7 shows a standard curve comparing the actual thickness (in nm) of the SiO2 thin film standards to the thickness determined using the methods disclosed herein.

FIG. 7 shows a standard curve comparing the actual thickness (in nm) of the $SiO_2$ standards to the thickness determined using the methods disclosed herein. As can be seen, the values obtained using the disclosed methods closely match the actual thicknesses of the silicon dioxide standards. These are excellent results, with only a 1.8 nm error on average, maximum error of 3.6 nm and standard curve and slope =1.0014 and 1.9156 nm, respectively, demonstrating that the basic mathematics of the disclosed methods are correct. The observed absolute error results are expected to decrease with higher scan-number values for each standard and longer scan times.

Table 3 shows the results of experiments with tear film interferometry spectra and demonstrates that using a starting value for the tear film lipid layer thickness (i.e. the a-term) which is too far from the actual lipid thickness value can produce incorrect results. Lipid thickness values for these spectra were verified with the '557 method. Starting values for the b-term in all cases were 0.66. Spectrum subj18rt11 is that of a tear film during Oasys contact lens wear, indicating that the method of the present invention is suitable for measuring tear film lipid layers during contact lens wear.

TABLE 3

| Spectrum | Statistica lipid thickness result, nm | Statistica b-term result | Stat lipid starting thickness (a-term, nm) |
|---|---|---|---|
| sub7base#49 | 82.17 | 0.2738 | 50, 90, 100 ok |
| sub1#118 | 25.26 | 0.9987 | 65, 75 ok; 100 no: 130.79 w b = .4416 |
| sub2AY | 51.99 | 0.9949 | 40, 50, 65, 75 ok; 100 no: 102.95 w b = .6396 |
| sub21#43 | 31.78 | 0.3701 | 40, 50, 65, 70 ok; 75 no: 110.86 w b = .1828 |
| sub2CV | 78.18 | 0.9974 | 50, 65, 75, 100 ok |
| subj18rt11 | 7.94 | 0.9322 | 65 ok; 73, 100 no: 132.28 w b = .3757 |

Figure 8:
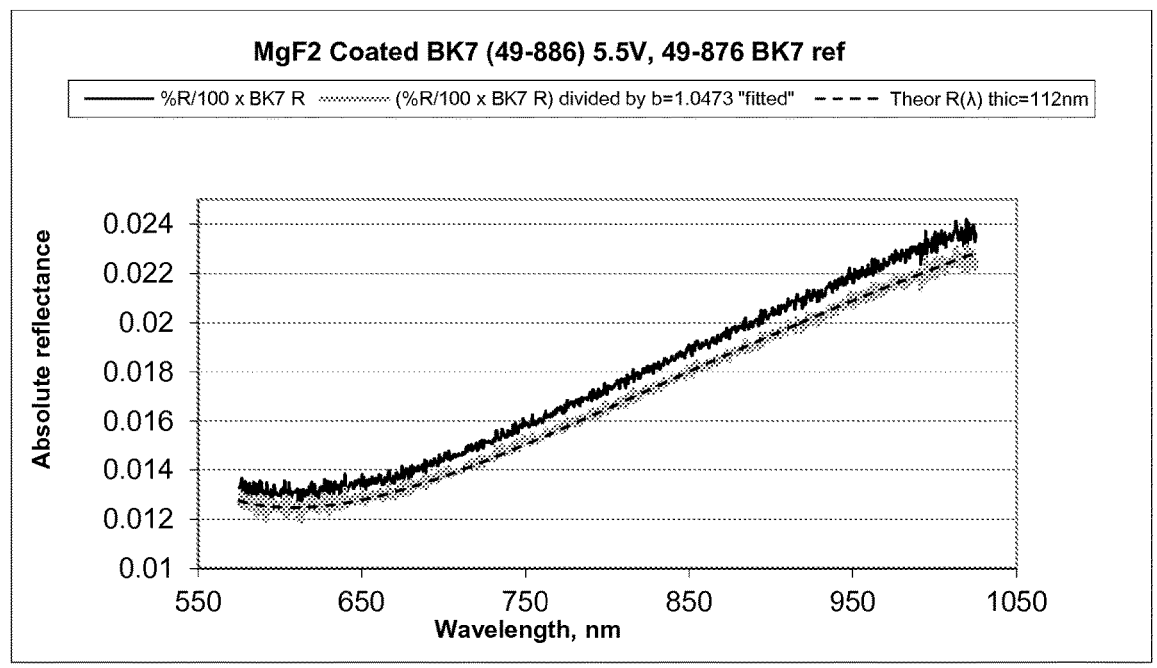
FIG. 8 shows a theoretical spectrum (dashed line, ----) vs. b-term fitted spectrum (light grey line, overlapping dashed line) and spectrum without the b-term fit (black line).

FIG. 8 shows the results of using the methods disclosed herein to measure a thin $MgF_2$ film on a curved BK7 lens surface. This sample serves as a surrogate for a human tear lipid film on the curved aqueous corneal surface. The results show the $MgF_2$ film to be 111.98 nm thick. Here, the b-term started at 1 and converged to a value of 1.0473. The measured and theoretical spectra overlay one another exactly, further confirming the method herein. FIG. 8 shows a theoretical spectrum (dashed line, ----) vs. b-term fitted spectrum (light grey line, overlapping dashed line) and spectrum without the b-term fit (black line). Materials: $MgF_2$-coated BK7 lens, Edmund Optics (Barrington N.J. 08007) part 49-886, radius of curvature=7.75 mm, used with uncoated BK7 ref. lens, Edmund Optics part 49-876, radius of curvature=7.75 mm.

Given that the above results were obtained using the novel methods disclosed herein, there is potential uncertainty as to whether the $MgF_2$ film thickness is 111.98 nm. Thus, a more rigorous method confirmation experiment was conducted using a 12.7 mm diameter, 7.75 mm radius of curvature $MgF_2$-coated plano-convex BK7 lens (Edmunds part no. 49-855). Using the methods disclosed herein with an interferometer light source voltage of 5.5V, the $MgF_2$ coating thickness was measured on both sides. The convex side was measured using a 7.75 mm radius of curvature uncoated BK7 lens as reference and the b-term mathematics process

TABLE 2

Figure 9:
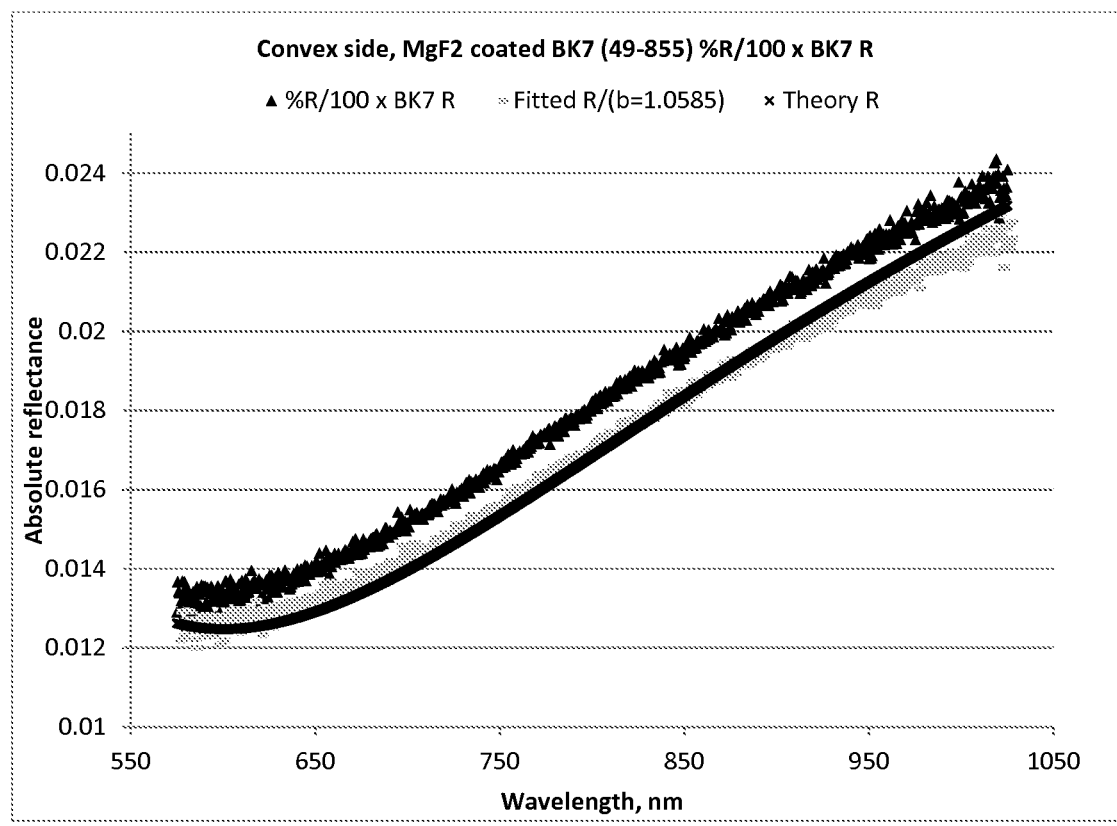
FIGS. 9 and 10 show calculated absolute reflectance spectra for the $MgF_2$ coating on the convex (FIG. 9) and the flat (FIG. 10) faces of a coated BK7 lens, both compared to a calculated theoretical spectrum for the $MgF_2$ coating.
Figure 10:
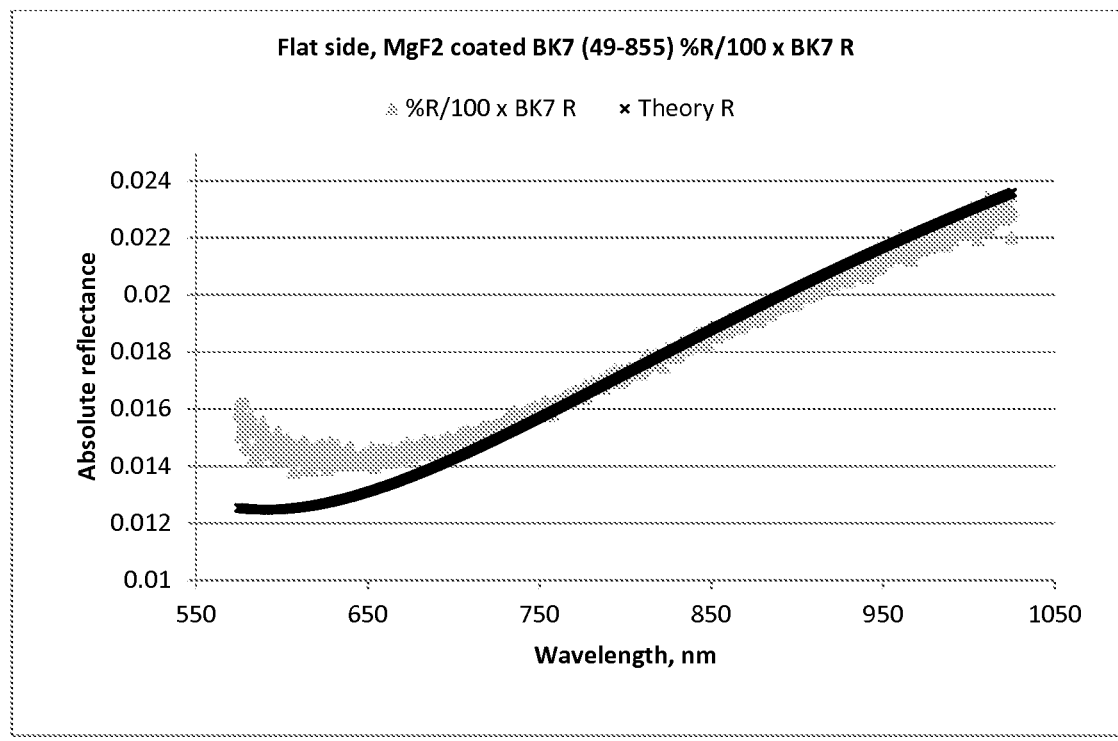

| Actual SiO2 Thickness, nm | STAT Input | | Meas. SiO2 Thickness, nm | Avg. Meas. SiO2 Thickness, nm | B |
|---|---|---|---|---|---|
| 0 | 65 | a | 4.42 | | |
| | 0.66 | b | | | 1.002 |
| 48.26 | 65 | a | 47.57 | 48.12 | |
| | 0.66 | b | | | 1.026 |
| 48.26 | 65 | a | 48.37 | | |
| | 0.66 | b | | | 0.994 |
| 48.26 | 65 | a | 48.43 | | |
| | 0.66 | b | | | 1.035 |
| 95.01 | 65 | a | 98.54 | 98.56 | |
| | 0.66 | b | | | 1.062 |
| 95.01 | 65 | a | 98.57 | | |
| | 0.66 | b | | | 1.062 |
| 95.01 | 65 | a | 98.55 | | |
| | 0.66 | b | | | 1.063 |
| 188.58 | 200 | a | 190.53 | 190.55 | |
| | 0.66 | b | | | 1.033 |
| 188.58 | 200 | a | 190.55 | | |
| | 0.66 | b | | | 1.032 |
| 188.58 | 200 | a | 190.56 | | |
| | 0.66 | b | | | 1.030 | was employed. The plano (flat) side was measured using a flat uncoated BK7 reference lens. The thickness calculations for flat samples do not always require the use of the b-term. The b-term is useful when employing flat references when the reference surface is not placed orthogonally to the incident light from the interferometer. Otherwise, the mathematics are identical to those used for curved surfaces. FIGS. 9 and 10 present the results. In FIG. 9, Dark triangles=%R/100×BK7 R; Light lines=Fitted R/(b=1.0585); and Dark ×=Theory R. In FIG. 10, Light triangles=%R/100×BK7 R; and Dark ×=Theory R.

The methods herein determined $MgF_2$ coating thicknesses to be 110.49 nm and 108.73 nm for the convex and flat sides, respectively. This is consistent with the assumption that the convex and flat surfaces were coated identically. As a further confirmation of the thickness of the $MgF_2$ coating, a spectroscopic Ellipsometer (model alpha SE, J. A. Woollam, Lincoln, Nebr. 68508-2243) was employed to measure thickness of the coating on the flat surface. However, the convex surface coating could not be measured with the ellipsometer due to beam geometry requiring flat samples. The ellipsometer measured a coating thickness for the flat surface of 110.0±0.64 nm, in excellent agreement with the interferometer result of 108.73 nm for this surface (Δthickness=1.27 nm). Since ellipsometer measurements are considered correct within thin film technology hierarchy, and both the convex and flat surfaces are assumed to have identical coating thicknesses, the b-term method for thin films on curved surfaces has been additionally verified to have an error of only about 1 nm.

Figure 11:
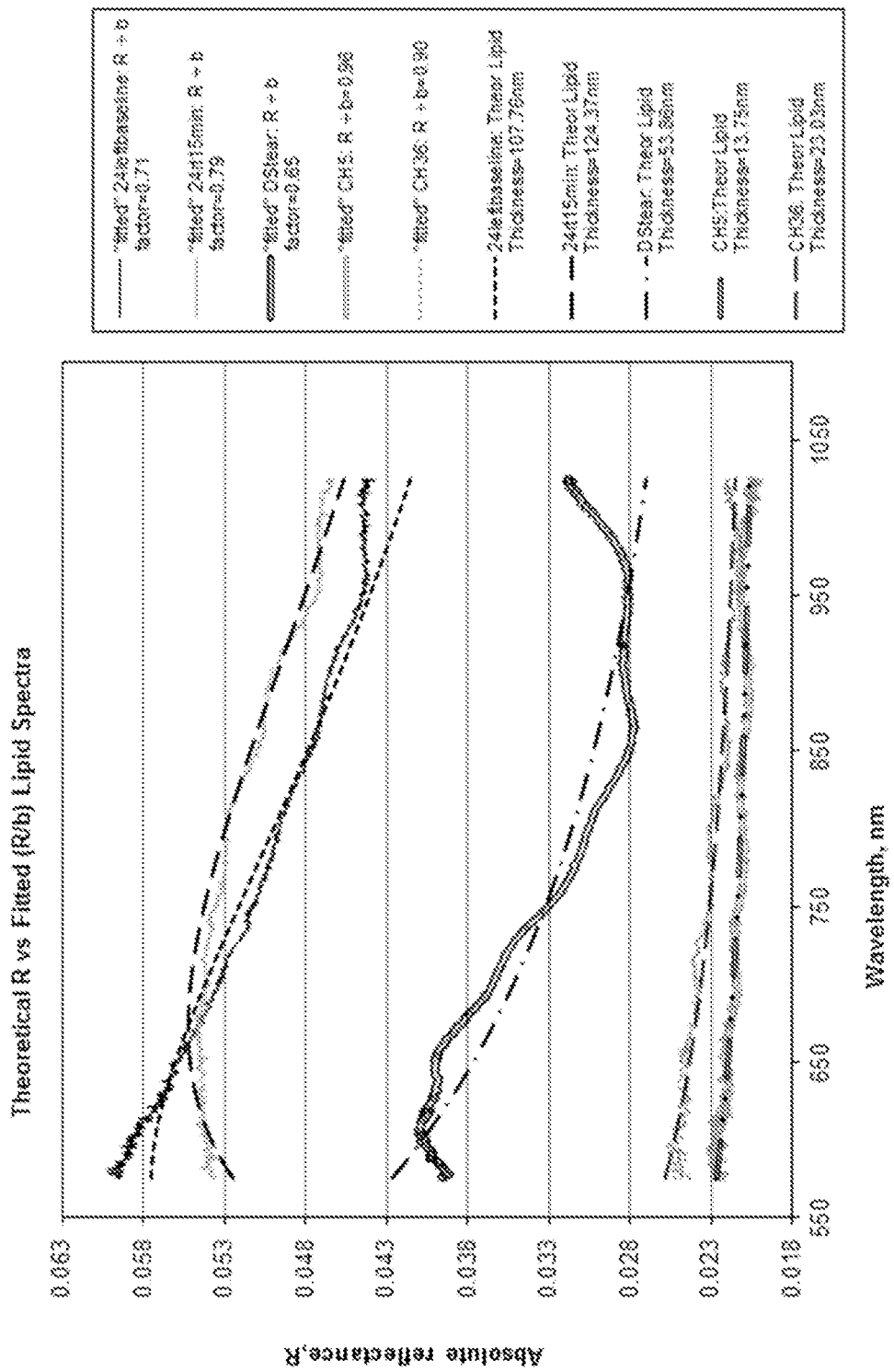
FIG. 11 shows calculated absolute reflectance spectra for tear film lipid spectra compared to calculated theoretical spectra.

Finally, the previously developed Statistica software program was applied to tear film lipid spectra, where the input data are $v5=R(\lambda)$ meas tear lipid sample×$R(\lambda)$ abs BK7 reference (BK7 abs R calc)/100 and where $v1=n_0$ air=1, $v2=n_1(\lambda)$ lipid, $v3=n_2(\lambda)$ aqueous, $v4$=measured $\lambda$, the variable 'a' is the fitted lipid film thickness, and the variable 'b' is the final correction term which moves the measured spectrum up or down on the theoretical R axis (y-axis) to achieve a match with theory (FIG. 11).

The measured spectra in FIG. 11 were plotted by dividing v5 by the fitted b-term at each wavelength. FIG. 11 shows lipid film thicknesses varying from 13.75 nm to 23.03 nm, 53.86 nm, 107.76 nm and 124.37 nm. It should be noted that the tear spectra in FIG. 11 include cosine-function oscillations from the aqueous layer (the smaller oscillations). These can be subtracted using a modified software program. Also, it is clear from the spectrum of the 188.6 nm SiO2 standard (not shown), that spectral data beyond 950-1000 nm may involve some optical error, perhaps from optical aberration. The spectrum of the 48.26 nm $SiO_2$ standard used with the curved BK7 reference in FIG. 7 also shows some optical error above 950-1000 nm. Thus, a refined software program may delete data beyond 950 nm. Nonetheless, it is seen that the lipid spectra match the theoretical spectra very well. Note, these spectra were acquired over 504 msec, to simultaneously measure the aqueous layer. It is known that the lipid layer thickness may change over this time interval. This can cause measured spectra such as the 53.86 nm spectrum to deviate somewhat from theory. In various embodiments, spectra will be acquired in intervals as short as 20-100 msec to resolve this question. Alternatively, the shape of the 53.86 nm spectrum may arise from lipid film thickness variation within the 133 um × 12.5 um spot. In various embodiments, the spot size will be reduced to resolve this question.

A modified Statistica software program was created, using a series of input values, where the input data are v6-v155= $R(\lambda)$ meas tear lipid samples and where $v1=n_0$ air=1, $v2=n_1(\lambda)$ lipid, $v3=n_2(\lambda)$ aqueous, $v4$=measured $\lambda$ and where $v5=R(\lambda)$ abs BK7 reference (BK7 abs R calc)/100 and where the variable a=the fitted lipid film thickness and the variable b=the final correction term which moves the measured spectrum up or down on the theoretical R axis (y-axis) to achieve a match with theory. Here the Euler equation becomes:

$$v6-v155=(1-((8*v1*v2**2*v3)/((v12+v22)*\\(v22+v32))+4*v1*v2**2*v3+((v12-\\v22)*(v22-v32)*(\cos\\(4*3.14159*v2*a*0.98666/v4))))))*b/v5.$$

Statistica software program code follows for the first several spectrum calculations (v6 and v7). Here, the starting value for lipid thickness=65 nm=a-term starting value. The b-term starting value is set to 0.66. Measured spectra wavelength is edited to 575-950 nm:

```
S1.DeleteCases 1, 30 and S1.DeleteCases 730, 994
Option Base 1
Sub Main
Dim AO As AnalysisOutput
Dim AWB As Workbook
Dim S1 As Spreadsheet
Set S1 = ActiveDataSet
S1.DeleteCases 1, 30
S1.DeleteCases 730, 994
Dim newanalysis2 As Analysis
Set newanalysis2 = Analysis (scNonlinearEstimation, S1)
With newanalysis2.Dialog
    .NonlinearMethod = scNlnUserSpecifiedRegressionLeastSquares
End With
newanalysis2.Run
With newanalysis2.Dialog
    .UserFunction = "v6 = ((1-
((8*v1*v2**2*v3)/((v1**2+v2**2)*(v2**2+v3**2)+
4*v1*v2**2*v3+ ((v1**2-v2**2)*(v2**2-v3**2)*
(cos(4*3.14159*v2*a*0.98666/v4))))))*b/v5"
    .CasewiseDeletionOfMD = True
End With
newanalysis2.Run
With newanalysis2.Dialog
    .EstimationMethod = scNlnLevenbergMarquardt
    .MaxNumberOfIterations = 50
    .ConvergenceCriterion = 6
    .StartValues = "65 .66 "
End With
newanalysis2.Run
With newanalysis2.Dialog
    .AlphaForLimits = 95
    .PLevelForHighlighting = 0.05
End With
Set AO = newanalysis2.RouteOutput(newanalysis2.Dialog.Summary)
AO.Visible = True
If AO.HasWorkbook Then
        Set AWB = AO.Workbook
Else
        Set AWB = Nothing
End If
newanalysis2.GoBack
With newanalysis2.Dialog
    .UserFunction = "v7 = ((1-
((8*v1*v2**2*v3)/((v1**2+v2**2)*(v2**2+v3**2)+
4*v1*v2**2*v3+ ((v1**2-v2**2)*(v2**2-v3**2)*
(cos(4*3.14159*v2*a*0.98666/v4))))))*b/v5"
    .CasewiseDeletionOfMD = True
End With
newanalysis2.Run
With newanalysis2.Dialog
    .EstimationMethod = scNlnLevenbergMarquardt
    .MaxNumberOfIterations = 50
    .ConvergenceCriterion = 6
    .StartValues = "65 .66 "
End With
newanalysis2.Run
With newanalysis2.Dialog
    .AlphaForLimits = 95
```

```
    .PLevelForHighlighting = 0.05
End With
Set AO = newanalysis2.RouteOutput(newanalysis2.Dialog.Summary)
AO.Visible = True
If AO.HasWorkbook Then
        Set AWB = AO.Workbook
Else
        Set AWB = Nothing
End If
```

The remaining program code follows the above repeating sequence for additional spectra calculations.

A sample portion of the v1-v6 inputs for a single spectrum (columns 1-6, left to right, where v6=measured % reflectance for tear lipid spectrum #1) follows in Table 4. Note these columns extend to the last measured wavelength (1085.11 nm, not shown), and the first 30 rows (shown as input data examples here) and rows where λ≥950.6843 nm are deleted by the software.

TABLE 4

| | | | | | |
|---|---|---|---|---|---|
| 1 | 1.48173057 | 1.33783826 | 559.409653 | 0.00042340272 | 36.8916 |
| 1 | 1.48165317 | 1.33782012 | 559.929243 | 0.000423370425 | 36.1339 |
| 1 | 1.48157604 | 1.33780203 | 560.448833 | 0.000423338215 | 36.167 |
| 1 | 1.48149916 | 1.33778399 | 560.968423 | 0.00042330609 | 36.2099 |
| 1 | 1.48142254 | 1.337766 | 561.488013 | 0.000423274049 | 36.5871 |
| 1 | 1.48134618 | 1.33774806 | 562.007604 | 0.000423242093 | 36.8416 |
| 1 | 1.48127008 | 1.33773018 | 562.527194 | 0.000423210221 | 36.2501 |
| 1 | 1.48119423 | 1.33771234 | 563.046784 | 0.000423178432 | 36.5386 |
| 1 | 1.48111863 | 1.33769455 | 563.566375 | 0.000423146727 | 35.974 |
| 1 | 1.48104329 | 1.33767681 | 564.085965 | 0.000423115104 | 35.8217 |
| 1 | 1.48096819 | 1.33765911 | 564.605555 | 0.000423083565 | 35.6451 |
| 1 | 1.48089335 | 1.33764147 | 565.125145 | 0.000423052107 | 35.7768 |
| 1 | 1.48081875 | 1.33762388 | 565.644736 | 0.000423020732 | 35.82 |
| 1 | 1.48074441 | 1.33760633 | 566.164326 | 0.000422989438 | 35.8625 |
| 1 | 1.48067031 | 1.33758883 | 566.683916 | 0.000422958225 | 35.8153 |
| 1 | 1.48059646 | 1.33757138 | 557.203506 | 0.000422927093 | 35.9704 |
| 1 | 1.48052285 | 1.33755398 | 557.723096 | 0.000422896042 | 35.9033 |
| 1 | 1.48044948 | 1.33753663 | 568.242687 | 0.000422865072 | 35.8368 |
| 1 | 1.48037636 | 1.33751932 | 568.762277 | 0.000422834181 | 35.5937 |
| 1 | 1.48030348 | 1.33750206 | 569.281867 | 0.00042280337 | 35.6052 |
| 1 | 1.48023084 | 1.33748485 | 569.801457 | 0.000422772638 | 35.6605 |
| 1 | 1.48015843 | 1.33746768 | 570.321048 | 0.000422741985 | 35.3016 |
| 1 | 1.48008627 | 1.33745056 | 570.840638 | 0.000422711411 | 35.7279 |
| 1 | 1.48001434 | 1.33743349 | 571.360228 | 0.000422680916 | 35.6287 |
| 1 | 1.4799428 | 1.3374165 | 571.878762 | 0.00042265056 | 35.2528 |
| 1 | 1.47987134 | 1.33739952 | 572.398352 | 0.00042262022 | 34.7073 |
| 1 | 1.47980012 | 1.33738259 | 572.917943 | 0.000422589957 | 35.3448 |
| 1 | 1.47972913 | 1.3373657 | 573.437533 | 0.000422559772 | 35.0115 |
| 1 | 1.47965838 | 1.33734886 | 573.957123 | 0.000422529664 | 35.5492 |
| 1 | 1.47958785 | 1.33733207 | 574.476713 | 0.000422499632 | 35.069 |
| 1 | 1.4795177 | 1.33731535 | 574.995248 | 0.000422469737 | 35.1151 |
| 1 | 1.47944763 | 1.33729865 | 575.514838 | 0.000422439857 | 34.7243 |

Figure 12:
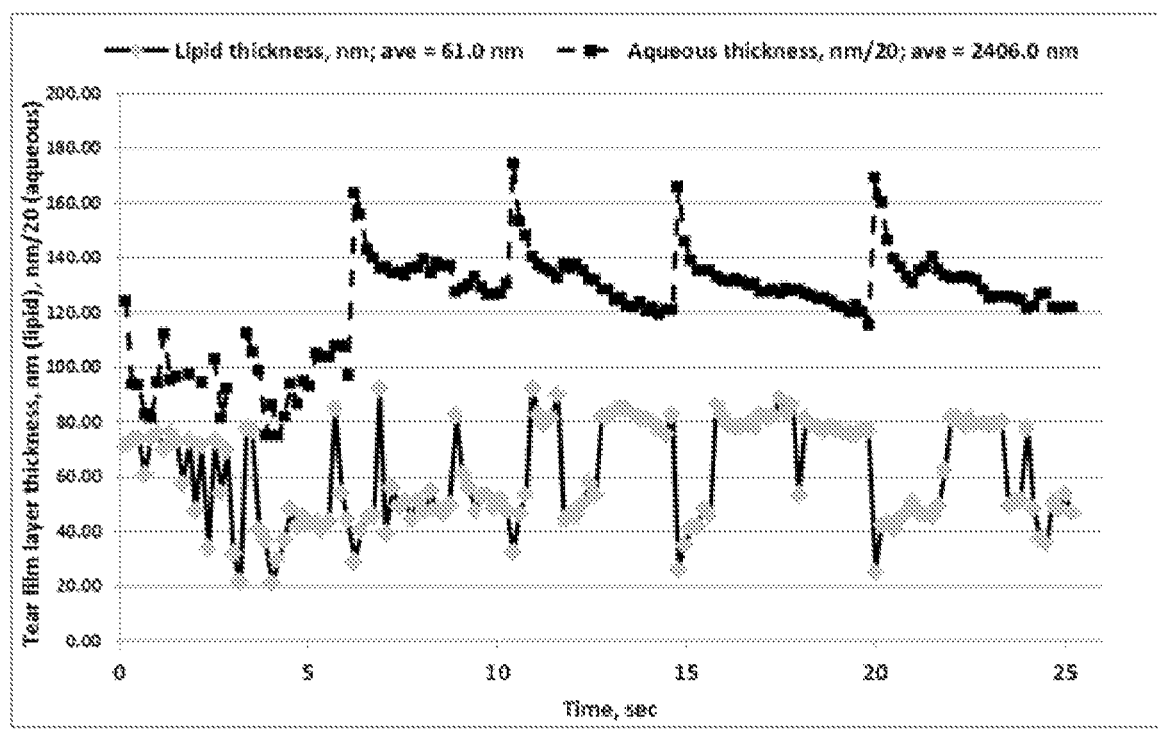
FIG. 12 shows thicknesses of the lipid (diamonds) vs. aqueous (squares) tear film layers during blinking (downward spikes in lipid thickness measurements) of the subject's eyelids.

FIG. 12 illustrates the results of using the lipid thickness method herein to measure tear lipid layer thickness 150× over a 25.2 second period. It was found that in a few cases, a 65 nm starting value for the a-term resulted in a correct, but negative value, for the thickness. In any case, such results occur infrequently. A test of the current method with these 150 spectra produced only 5 such results (3.3%), which is considered acceptable. It is not currently known why correct values with negative signs are observed. All of the negative-sign results observed thus far have occurred with lipid layer thickness values less than 39.45 nm, which are further away from the 65 nm starting value than many spectra. In any case, positive-value results are obtained for the aforementioned negative-value spectra by using a lower starting value for the a-term. Aqueous layer thickness and blinking were measured simultaneously according to known methods. Blinks are easily visualized by the spiking in the aqueous layer thickness at the same time as the blink. This technological capability to accurately and quickly measure the tear film lipid layer has not previously been demonstrated. The results show that the lipid layer averages 61.0 nm and thickens on average about 50 nm very quickly after a blink, within on average 0.588 seconds. These results are generally consistent with Korb, et. al, (Korb, DR, et. al. Tear Film Lipid Layer Thickness as a Function of Blinking. *Cornea* 13 (4):354-359. 1994), who showed that individuals with a lipid layer thickness of 75-150 nm demonstrated a mean increase in lipid layer thickness of 33 nm following forceful blinking. They are also consistent with Goto, et. al, (Goto, E and Tseng, C G. Differentiation of Lipid Tear Deficiency Dry Eye by Kinetic Analysis of Tear Interference Images. *Arch Ophthalmol.* Vol. 121, feb 2003, 173-180.), who showed that for those with 75 nm lipid films, mean lipid spread time following a blink was 0.36±0.22 seconds. FIG. 12 shows that contrary to one conventional theory, lipid layer thickening following a blink does not precede aqueous layer thickening. However, this is a single small test of the technology, and not a rigorous test of tear film spreading theory.

In various embodiments, the disclosed methods may be carried out on a computing system in communication with an interferometer (e.g. a wavelength-dependent interferometer). The computing system may include one or more computer systems in communication with one another through various wired and wireless communication means which may include communications through the Internet and/or a local network (LAN). Each computer system may include an input device, an output device, a storage medium (including non-transient computer-readable media), and a processor such as a microprocessor. Possible input devices include a keyboard, a computer mouse, a touch screen, and the like. Output devices include a cathode-ray tube (CRT) computer monitor, a LCD or LED computer monitor, and the like. Storage media may include various types of memory such as a hard disk, RAM, flash memory, and other magnetic, optical, physical, or electronic memory devices. The processor may be any suitable computer processor for performing calculations and directing other functions for performing input, output, calculation, and display of data in the disclosed system. Implementation of the computing system may include generating a set of instructions and data that are stored on one or more of the storage media and operated on by a controller. Thus, one or more controllers may be programmed to carry out embodiments of the disclosed invention. The data associated with the system may include image data, numerical data, or other types of data.

Conclusion

Novel mathematical algorithms and software methods have been independently developed to calculate absolute-reflectance of tear film lipid layers from measured tear film lipid layer reflectance using wavelength-dependent optical interferometry. The absolute reflectance measurements are used for the accurate and quick determination of lipid layer thickness. These algorithms are consistent with optical theory, with the exception of a single b-term, which may be empirically explained by light reflection from a curved surface or from non-orthogonal placement of a flat surface or from out-of-focus light reflection.

Thickness errors for the methods herein for thin films on curved surfaces in perfect focus are only a few nanometers (nm). In practice, collecting ≥50 tear lipid measurements, deleting out-of-focus spectra, and averaging the remaining spectra will keep lipid thickness errors small.

These methods are suitable for the quantitative evaluation of the effects of novel dual-function lipid-supplementation tear formulas on the tear film lipid layer. They are also useful for evaluating the effects of other eye drops, ophthalmic dry eye drugs and MPS solutions, and contact lenses on the tear film lipid layer.

Novel features of the present disclosure include the use of the expanded Euler equation with interferometer-dependent wavelength selection of wavelength-dependent Sellmaier equation-fitted complex refractive indices in the software program to calculate tear film lipid layer thickness, where v6, the measured reflectance variable R(λ) in an expanded Euler equation, is known and the actual lipid thickness d becomes the fitted lipid film thickness variable "a" (e.g., variable reversal in the expanded Euler equation) and wherein the expanded Euler equation also has a variable b, which is the final correction term which mathematically adjusts measured reflectance R (moves the measured spectrum up or down on the theoretical R axis (y-axis)) to achieve a match with theory:

$$v6=(1-((8*v1*v2**2*v3)/((v12+v22)*(v22+v32)+4*v1*v2**2*v3+((v12-v22)*(v22-v32)*(\cos(4*3.14159*v2*a*0.98666/v4))))))*b/v5.$$

where
v1=$n_0$ air=1,
v2=$n_1$ (λ) lipid (Sellmeier-form),
v3=$n_2$ (λ) aqueous,
v4=measured λ, and
v5=R(λ) abs BK7 reference (BK7 abs R calc)/100 and
wherein a Levenberg-Marquardt algorithm is used with a novel software program and a starting value for the a-term of 65 nm and for the b-term between 0 and 1.30 so that the program achieves the correct thickness and wherein spectral data without optical aberration between 575-950 nm are most preferred.

Other novel features include a method wherein a tear film lipid spectrum and slope is evaluated and a tear lipid layer thickness is estimated and this thickness estimate is thereafter used as the starting value for the a-term in the method above.

REFERENCES

The following references are herein incorporated by reference in their entirety:

Scaffidi, R C, Korb, R. Comparison of the Efficacy of Two Lipid Emulsion Eyedrops in Increasing Tear Film Lipid Layer Thickness. Eye & Contact Lens: Science & Clinical Practice, 2007; 33(1):38-44.

Goto, et al. Computer-Synthesis of an Interference Color Chart of Human Tear Lipid Layer, by a Colorimetric Approach. Invest. Ophthalmol. Vis. Sci., 2003;44:4693-4697.

Tiffany, J M. Refractive index of meibomian and other lipids. Current Eye Research, 5 (11), 1986, 887-889.

Stenzel, O. The Physics of Thin Film Optical Spectra. Editors: G. Ertl, H. Luth and D. Mills. Springer-Verlag Berlin Heidelberg 2005: 71-98.

Schott technical information document TIE-29 (2005).

Korb, D R, et. al. Tear Film Lipid Layer Thickness as a Function of Blinking. Cornea 13 (4):354-359. 1994.

Goto, E and Tseng, CG. Differentiation of Lipid Tear Deficiency Dry Eye by Kinetic Analysis of Tear Interference Images. Arch Ophthalmol. Vol. 121, feb 2003, 173-180.

Various features and advantages of the invention are set forth in the following claims.

What is claimed is:

1. A method of determining tear film lipid layer thickness, comprising the steps of:

measuring a tear film aqueous plus lipid layer relative reflectance spectrum of an ocular tear film using a wavelength-dependent optical interferometer, comprising:

measuring relative reflectance from a reference material;

measuring relative reflectance from the ocular tear film;

determining the tear film aqueous plus lipid layer relative reflectance spectrum of the ocular tear film based on the measured relative reflectance from the reference material and the measured relative reflectance from the ocular tear film;

converting the measured tear film aqueous plus lipid layer relative reflectance spectrum of the ocular tear film to a calculated absolute reflectance spectrum of the ocular tear film, wherein the calculated absolute reflectance spectrum is calculated based on wavelength-dependent refractive indices for air, lipid, and aqueous phases, comprising:

calculating the absolute reflectance spectrum of the ocular tear film based on the measured tear film aqueous plus lipid layer relative reflectance spectrum and an absolute reflectance of the reference material, for each of a plurality of wavelengths in the wavelength-dependent optical interferometer; and comparing the calculated absolute reflectance spectrum of the ocular tear film to a theoretical absolute reflectance lipid spectrum to determine a tear film lipid layer thickness, comprising:

iteratively comparing the calculated absolute reflectance spectrum of the ocular tear film to the theoretical absolute reflectance lipid spectrum for each of the plurality of wavelengths.

2. The method of claim 1, comprising determining the tear film aqueous plus lipid layer relative reflectance spectrum of the ocular tear film based on dividing the measured relative reflectance from the ocular tear film by the measured relative reflectance from the reference material.

3. The method of claim 2, further comprising dividing the determined tear film aqueous plus lipid layer relative reflectance spectrum by a correction factor to correct for differences between the theoretical absolute reflectance lipid spectrum and the calculated absolute reflectance spectrum.

4. The method of claim 3, wherein the correction factor is 100.

5. The method of claim 1, comprising calculating the absolute reflectance spectrum of the ocular tear film, by multiplying the measured tear film aqueous plus lipid layer relative reflectance spectrum times the absolute reflectance of the reference material, for each of the plurality of wavelengths in the wavelength-dependent optical interferometer.

6. The method of claim 1, wherein comparing the calculated absolute reflectance spectrum of the ocular tear film to the theoretical absolute reflectance lipid spectrum further comprises selecting the minimum of a sum of least square differences between the calculated absolute reflectance spectrum of the ocular tear film and the theoretical absolute reflectance lipid spectrum for each of the plurality of wavelengths.

7. The method of claim 6, wherein minimizing the sum of least square differences comprises using a Levenburg-Marquardt algorithm.

8. The method of claim 1, wherein the wavelength-dependent refractive indices for lipid are based upon a Sellmeier equation form.

9. The method of claim 1, wherein the reference material comprises a reference lens.

10. The method of claim 9, wherein the reference lens has a radius of curvature of 7.75 mm.

11. The method of claim 8, comprising iteratively comparing the calculated absolute reflectance spectrum of the ocular tear film to the theoretical absolute reflectance lipid spectrum for each of the plurality of wavelengths for a 65 nm thick lipid layer.

12. A system for determining tear film lipid layer thickness, comprising:
 a wavelength-dependent optical interferometer; and
 a controller in communication with the wavelength-dependent optical interferometer, the controller configured to:
  measure a tear film aqueous plus lipid layer relative reflectance spectrum of an ocular tear film using the wavelength-dependent optical interferometer, comprising:
   measuring relative reflectance from a reference material;
   measuring relative reflectance from the ocular tear film;
   determining the tear film aqueous plus lipid layer relative reflectance spectrum of the ocular tear film based on the measured relative reflectance from the reference material and the measured relative reflectance from the ocular tear film;
  convert the measured tear film aqueous plus lipid layer relative reflectance spectrum of the ocular tear film to a calculated absolute reflectance spectrum of the ocular tear film, wherein the calculated absolute reflectance spectrum is calculated based on wavelength-dependent refractive indices for air, lipid, and aqueous phases, comprising:
   calculating the absolute reflectance spectrum of the ocular tear film based on the measured tear film aqueous plus lipid layer relative reflectance spectrum and an absolute reflectance of the reference material, for each of a plurality of wavelengths in the wavelength-dependent optical interferometer; and
  comparing the calculated absolute reflectance spectrum of the ocular tear film to a theoretical absolute reflectance lipid spectrum to determine a tear film lipid layer thickness, comprising:
   iteratively comparing the calculated absolute reflectance spectrum of the ocular tear film to a theoretical absolute reflectance lipid spectrum for each of the plurality of wavelengths.

13. The system of claim 12, wherein the controller is configured to determine the tear film aqueous plus lipid layer relative reflectance spectrum of the ocular tear film based on dividing the measured relative reflectance from the ocular tear film by the measured relative reflectance from the reference material.

14. The system of claim 13, wherein the controller is further configured to divide the determined tear film aqueous plus lipid layer relative reflectance spectrum by a correction factor to correct for differences between the theoretical absolute reflectance lipid spectrum and the calculated absolute reflectance spectrum.

15. The system of claim 14, wherein the correction factor is 100.

16. The system of claim 12, wherein the controller is configured to calculate the absolute reflectance spectrum of the ocular tear film by being configured to multiply the measured tear film aqueous plus lipid layer relative reflectance spectrum times the absolute reflectance of the reference material, for each of the plurality of wavelengths in the wavelength-dependent optical interferometer.

17. The system of claim 12, wherein the controller is configured to compare the calculated absolute reflectance spectrum of the ocular tear film to the theoretical absolute reflectance lipid spectrum by being further configured to select the minimum of a sum of least square differences between the calculated absolute reflectance spectrum of the ocular tear film and the theoretical absolute reflectance lipid spectrum for each of the plurality of wavelengths.

18. The system of claim 12, wherein the wavelength-dependent refractive indices for lipid are based upon a Sellmeier equation form.

19. The system of claim 12, wherein the reference material comprises a reference lens.

20. The system of claim 19, wherein the reference lens has a radius of curvature of 7.75 mm.

21. The system of claim 12, wherein the controller is configured to iteratively compare the calculated absolute reflectance spectrum of the ocular tear film to the theoretical absolute reflectance lipid spectrum for each of the plurality of wavelengths for a 65 nm thick lipid layer.

* * * * *